(12) United States Patent
Doig et al.

(10) Patent No.: US 7,438,721 B2
(45) Date of Patent: Oct. 21, 2008

(54) UNIVERSAL MODULAR STENT GRAFT ASSEMBLY TO ACCOMMODATE FLOW TO COLLATERAL BRANCHES

(75) Inventors: Scott Doig, Santa Rosa, CA (US); James Machek, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 91 days.

(21) Appl. No.: 10/423,297

(22) Filed: Apr. 25, 2003

(65) Prior Publication Data

US 2004/0215327 A1    Oct. 28, 2004

(51) Int. Cl.
*A61F 2/04* (2006.01)
(52) U.S. Cl. .................. 623/1.15; 623/1.13; 623/1.16
(58) Field of Classification Search ............... 623/1.13, 623/1.15, 1.16, 1.35; 604/8
See application file for complete search history.

(56) References Cited

U.S. PATENT DOCUMENTS

| | | | |
|---|---|---|---|
| 5,456,712 A * | 10/1995 | Maginot | 623/1.13 |
| 5,617,878 A | 4/1997 | Taheri | 128/898 |
| 5,632,772 A | 5/1997 | Alcime et al. | |
| 5,775,772 A | 7/1998 | Lefranc | 297/250.1 |
| 5,906,640 A * | 5/1999 | Penn et al. | 623/1.15 |
| 5,984,955 A | 11/1999 | Wisselink | 623/1 |
| 6,056,775 A | 5/2000 | Borghi et al. | |
| 6,059,824 A | 5/2000 | Taheri | 623/1 |
| 6,203,568 B1 * | 3/2001 | Lombardi et al. | 623/1.13 |
| 6,258,115 B1 | 7/2001 | Dubrul | 606/200 |
| 6,261,273 B1 * | 7/2001 | Ruiz | 604/284 |
| 6,645,242 B1 * | 11/2003 | Quinn | 623/1.16 |
| 2002/0035392 A1 * | 3/2002 | Wilson | 623/1.11 |
| 2003/0045926 A1 | 3/2003 | Pinchasik | |

\* cited by examiner

*Primary Examiner*—Corrine McDermott
*Assistant Examiner*—Christopher D Prone
(74) *Attorney, Agent, or Firm*—Serge Hodgson

(57) ABSTRACT

Universal modular stented graft assemblies are assembled, on site, and often in a patient's parent artery, from at least two components; a first component and a second component. The first and second components each include a window, or fenestration. The second component couples with the first component by fitting at least partially in the first component to form the universal modular stent graft assembly with an adjustable collateral opening. As the first and second components are assembled, the first and second components are adjusted relative to each other so that the first and second component windows overlap to form a collateral opening whose size is selectable, depending on the overlap, with the desired position and dimensions in the universal modular stent graft assembly.

10 Claims, 14 Drawing Sheets

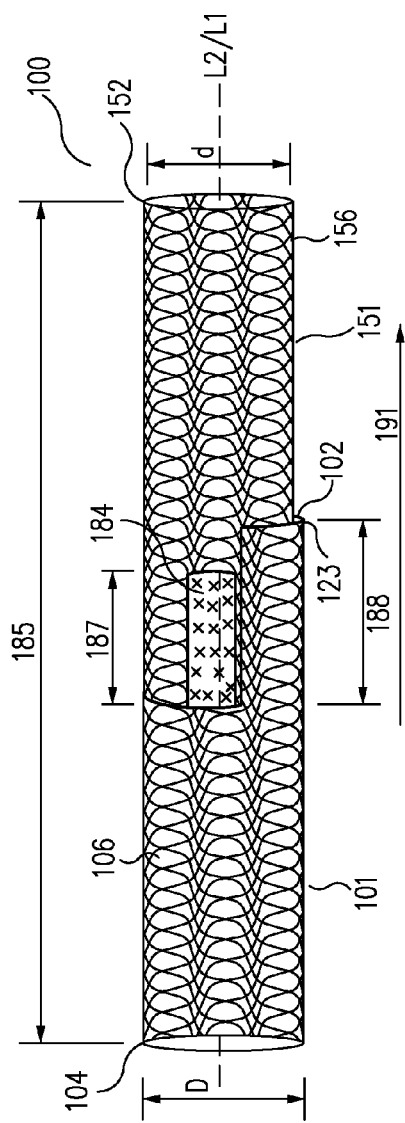
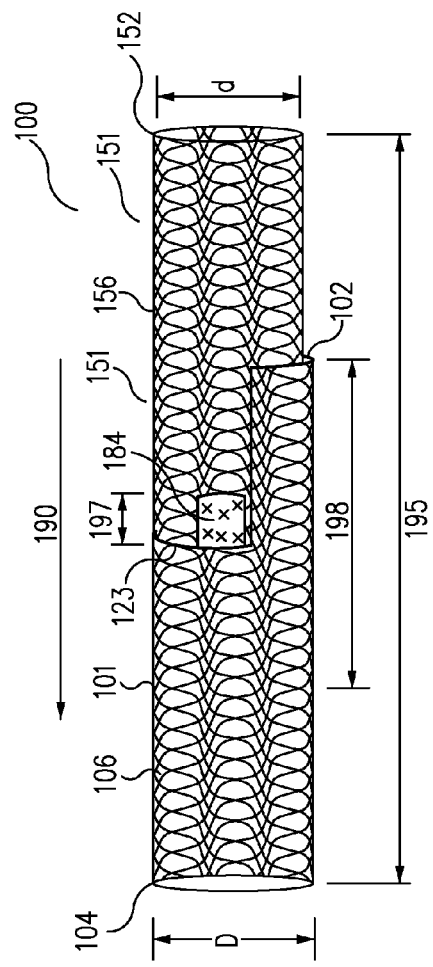
FIG. 1E
FIG. 1F

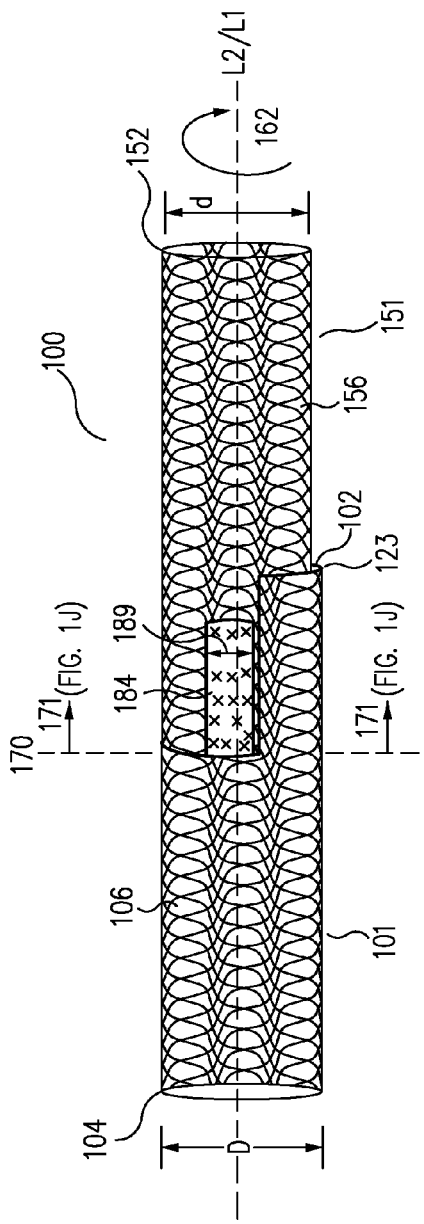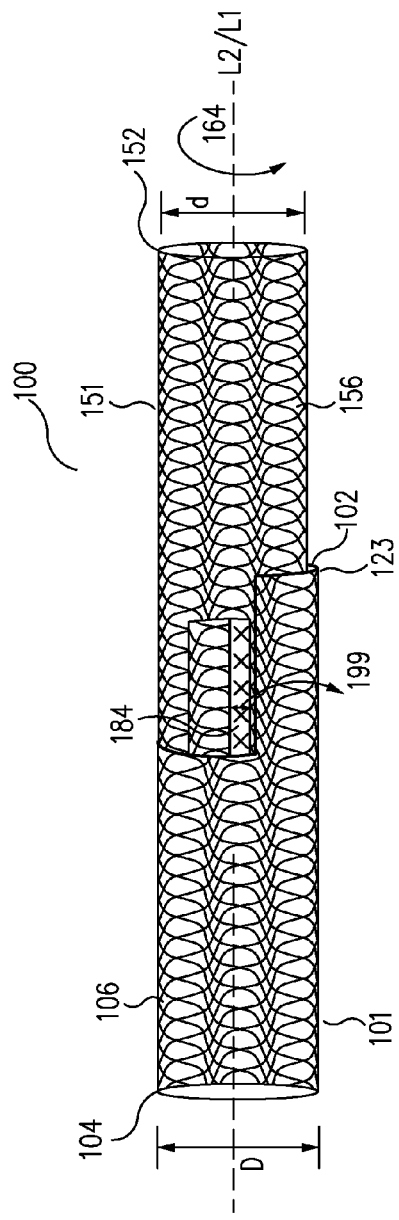

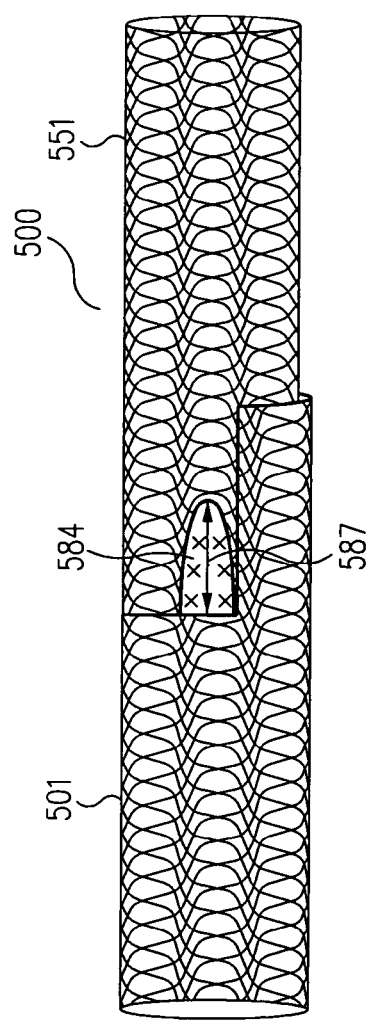
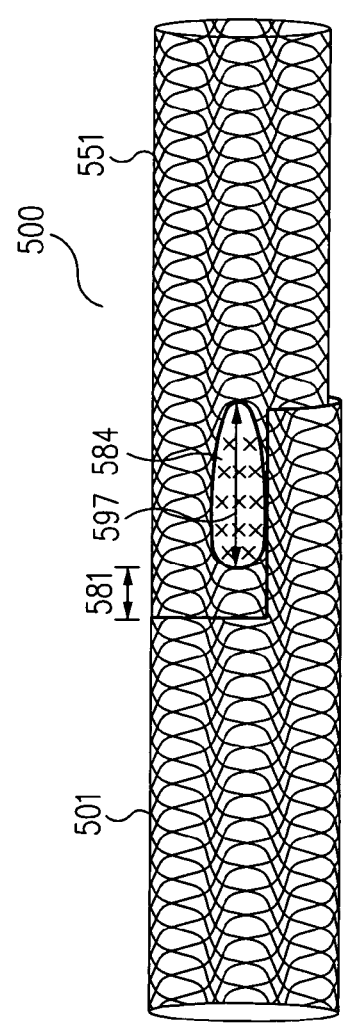

UNIVERSAL MODULAR STENT GRAFT ASSEMBLY TO ACCOMMODATE FLOW TO COLLATERAL BRANCHES

BACKGROUND OF THE INVENTION

1. Field of the Invention

The present invention relates generally to the treatment of arterial disease, including for example, aortic occlusive disease, and in particular, to a universal modular stent graft assembly and method for treating arterial disease at the intersection of two or more arteries or blood flow passageways such as the intersection of the aorta and renal arteries or the aorta and posterior spinal arteries 2. Description of the Related Art In the prior art, treatment of arterial disease was effected by various surgical techniques, some of which involved the use of stents and grafts. For example, it is well known in the art to interpose within the diseased portion of an artery a stent, whether made of stainless steel, nitinol or other materials capable of being balloon-expanded or self-expanded, for strengthening the walls of a stenotic or occluded artery. Grafts, comprised of hollow tubes of material such as Dacron, were normally inserted within the walls of a damaged artery and then sewn into position or expanded using a stented balloon catheter. It was also well known in the prior art to use a graft in conjunction with a stent to repair highly damaged portions of the aorta or other arteries thereby ensuring blood flow and reducing the risk of an aneurysm or rupture.

A more severe problem occurs when it is desirable to use a graft or a stented graft at or around the intersection of a major artery (e.g., the aorta) with intersecting collateral arteries (e.g., the renal arteries). While a stented graft could be used to strengthen and ensure the flow of blood through the aorta, the use of a stented graft could effectively seal or block off the blood flow to collateral organs, such as the kidneys. One technique for repairing weakened arterial walls is described in U.S. Pat. No. 5,617,878 to Taheri entitled "Stent and Method for Treatment of Aortic Occlusive Disease", also referred to herein as Taheri 878. According to Taheri 878, the treatment included placing a graft at the intersection of two arteries. A cutting device was then used to make an opening in the graft at a point corresponding to the intersection of the two arteries. According to Taheri 878, a stent was then inserted into the graft and through the graft opening; the stent having a cylindrical collar with tines that grabbed and caught the walls of the graft to attach the stent to the opening in the graft whereby the flow of blood at the intersection of the arteries was allowed. The use of a "bifurcated" stent comprised of a single stent and graft adapted through cutting to incorporate a second stent and graft is described in U.S. Pat. No. 5,755,772 to Evans et al.

The Taheri 878 and Evans et al. prior art techniques discussed above, while somewhat effective, were cumbersome and difficult to employ and execute. Consequently, Taheri went on to create another method and structure set forth in U.S. Pat. No. 6,059,824 to Taheri entitled "Coupled Main and Collateral Stent and Method For Treatment Of Arterial Disease", referred to herein as Taheri '824. According to Taheri '824, a stent assembly included first and second stents comprising a main graft and at least one intersecting collateral graft or, if desired, a main stented graft and at least one collateral stented graft for treating arterial disease at the intersection of various major arteries, e.g., the aorta and renal arteries or brachycephalic arteries. The method of Taheri '824 required first precisely measuring, through techniques such as ultrasound or other imaging, the exact location of the intersection of two arteries to be treated. To effectively use the method of Taheri '824, the size or diameter of the artery intersection point also needed to be precisely measured and the lateral opening of the main graft and the open end of the collateral graft had to be precisely sized so that once they were deployed and positioned in the respective main and collateral arteries, they would support the arteries at the point of intersection. According to Taheri '824, the main and collateral stented grafts were then coupled to each other with a system of detents and inlets, the detents of one being received in the inlets of the other to lock them together.

While Taheri '824 arguably provided some improvement over the Taheri 878 and Evans et al. prior art techniques discussed above, the method and structure of Taheri '824 shared significant drawbacks with Taheri 878 and Evans et al. For instance, as discussed above, Taheri '824 required a highly customized stented graft structure, that was "one of a kind", having precisely measured and implemented features such as the longitudinal distance between branches, the radial positioning of the openings, and diameters of the openings. Consequently, the custom stented graft structures used with prior art techniques such as Taheri '824 were, of course, not subject to mass production and were very labor intensive and expensive to produce.

Another drawback to the custom stented graft structures used with prior art techniques was that it was not always possible to obtain the exact measurements required to build the custom stented graft structures used because, even with modern imaging technology, it is not always possible to see, and precisely measure, every location in the human body. To complicate matters further, even if the exact measurements were, in theory, available, there was significant opportunity for the introduction of error in both the measurement taking process and the implementation of those measurements in the production of the custom stented graft structure.

In addition, because the custom stented graft structures used with prior art techniques were custom made, there was considerable time lag between diagnosis and deployment of the stented graft structure while waiting for the custom stented graft structure to be built. In addition, since the stented graft structures used with prior art techniques were custom made, the delivery and deployment mechanisms were also variable and subject to error and unanticipated complications.

In short, custom stented graft structures used with the prior art required precise measurement and production techniques, were vulnerable to error, and had to be special ordered well in advance of their use. Consequently, the custom stented graft structures used with the prior art were far from ideal and had significant limitations.

What is needed is a method and apparatus for treating arterial disease that can be more flexibly applied and can be used on short notice in a variety of situations and on a variety of patients.

SUMMARY OF THE INVENTION

In embodiments in accordance with the present invention, universal modular stented graft assemblies are assembled, on site, and often in a patient's parent artery, from at least two components; a first component and a second component. The first and second components each include a window, or fenestration. In one example, the second component has a diameter smaller than the diameter of the first component so that the second component couples with the first component by fitting at least partially in the first component to form the universal modular stent graft assembly.

As the first and second components are assembled, the first and second components are adjusted relative to each other so that the first and second component windows overlap to form an adjustable collateral opening in the universal modular stent graft assembly. By adjusting the relative longitudinal and radial positions of the first and second components the universal modular stent graft assembly, the longitudinal position of the adjustable collateral opening, the length of the adjustable collateral opening, the width of the adjustable collateral opening, and the radial positioning of the adjustable collateral opening can be varied to meet the needs of the particular application.

In particular, in one example, a first component of a universal modular stent graft assembly includes a proximal, or first, end and a distal, or second, end connected by a first component body. A first component longitudinal axis L1 runs through the first component body from the proximal end to the distal end. In one example, the distal end is substantially circularly cylindrical, as is the first component body, and the distal end and first component body have the same first diameter. In one example, the first component of the universal modular stent graft assembly includes a first component window, or fenestration.

In one embodiment in accordance with the present invention, the first component body of the universal modular stent graft assembly includes a stent body mesh made of stainless steel, nitinol, or other similar materials, adapted to render the first component flexible and, as well, capable of being reduced in dimension for insertion into various delivery devices such as a catheter or lumen and attendant balloon. In one example, the first component body of the universal modular stent graft assembly also includes a graft comprised of a hollow tube of material, such as Dacron, that is typically sewn into position or expanded through the use of a stented balloon catheter such that the stent body mesh and graft are coupled to form a hollow tubular structure making up the first component body.

In one example, a second component of a universal modular stent graft assembly includes a proximal, or first, end and a distal, or second, end connected by a second component body. A second component longitudinal axis L2 runs through second component body from the proximal end to the distal end. In one example, the distal end is substantially circularly cylindrical, as is the second component body, and the distal end and first component body have the same second diameter. In one example, the second diameter is smaller than the first diameter discussed above. In one example, the second component of the universal modular stent graft assembly includes a second component window, or fenestration.

In one embodiment in accordance with the present invention, the second component body of the universal modular stent graft assembly includes a stent body mesh made of stainless steel, nitinol, or other similar materials, adapted to render the second component flexible and, as well, capable of being reduced in dimension for insertion into various delivery devices such as a catheter or lumen and attendant balloon. In one example, the second component body of the universal modular stent graft assembly also includes a graft comprised of a hollow tube of material, such as Dacron, that is typically sewn into position or expanded through the use of a stented balloon catheter such that the stent body mesh and graft are coupled to form a hollow tubular structure making up the second component body.

As discussed above, in one example, the second diameter of the distal end and the body of the second component of the universal modular stent graft assembly is smaller than the first diameter of the proximal end of the first component of the universal modular stent graft assembly such that the distal end, and at least a portion of the body of the second component of the universal modular stent graft assembly, fits within the proximal end and at least a portion of the body of the first component of the universal modular stent graft assembly.

In one example, the second component is coupled with the first component to form the universal modular stent graft assembly by placing the distal end of the second component of the universal modular stent graft assembly inside the proximal end of the first component of the universal modular stent graft assembly such that the first component longitudinal axis L1 is coaxial with the second component longitudinal axis L2.

In one example, the first and second components are assembled into the universal modular stent graft assembly as the first and second components are deployed into a patient's parent artery. As discussed above, as the first and second components are deployed, the first and second components are adjusted relative to each other so that the first and second component windows overlap to form an adjustable collateral opening in the universal modular stent graft assembly. The relative longitudinal and radial positions of the first and second components of the universal modular stent graft assembly are varied as needed to adjust the longitudinal position of the adjustable collateral opening, the length of the adjustable collateral opening, the width of the adjustable collateral opening, and the radial positioning of the adjustable collateral opening to meet the needs of the particular application. In one example, these adjustments are made while the first and second components are being deployed into a patient's parent artery.

As discussed above, the longitudinal dimension, or length, of the collateral openings of the universal modular stented graft assemblies of the invention is adjustable and the longitudinal positioning of the openings is also adjustable. In addition, the radial dimension, or width, of the collateral openings of the universal modular stented graft assemblies of the invention is also adjustable, as is the radial positioning of the collateral openings. Consequently, in contrast to prior art methods and structures, the universal modular stented graft assemblies of the invention do not need to be custom made for each patient. Therefore, the universal modular stented graft assemblies of the invention can be mass-produced with minimal labor costs and kept in inventory on site until needed.

In addition, using the universal modular stented graft assemblies of the invention, it is not necessary to obtain the exact measurements that were required to build the custom stented graft structures used with prior art techniques. Consequently, there is less opportunity to introduse human error in both the measurement taking process and the implementing of those measurements during production/assembly/deployment.

In addition, in contrast to the prior art, using the universal modular stented graft assemblies of the invention, there is no production time lag since the universal modular stented graft assemblies of the invention can be kept in inventory and assembled on site and adjusted as needed.

For these and other reasons set forth in more detail below, the universal modular stented graft assemblies of the invention are a significant improvement over the prior art methods and structures.

BRIEF DESCRIPTION OF THE DRAWINGS

FIG. 1E is a side perspective-like view of the second component of FIG. 1B coupled with the first component of FIG. 1A to form a universal modular stent graft assembly, the universal modular stent graft assembly having been adjusted along its longitudinal axis to have an opening of a first length;

FIG. 1F is a side perspective-like view of the second component of FIG. 1B coupled with the first component of FIG. 1A to form a universal modular stent graft assembly, the universal modular stent graft assembly having been adjusted along its longitudinal axis to have an opening of a second length;

FIG. 1G is a side perspective-like view of the second component of FIG. 1B coupled with the first component of FIG. 1A to form a universal modular stent graft assembly, the universal modular stent graft assembly having been adjusted around its longitudinal axis to have an opening of a first width, and at a first radial position;

FIG. 1H is a side perspective-like view of the second component of FIG. 1B coupled with the first component of FIG. 1A to form a universal modular stent graft assembly, the universal modular stent graft assembly having been adjusted around its longitudinal axis to have an opening of a second width;

FIG. 5C is a side perspective-like view of the second component of FIG. 5B coupled with the first component of FIG. 5A to form a universal modular stent graft assembly;

FIG. 5D is a side perspective-like view of the second component of FIG. 5B coupled with the first component of FIG. 5A to form a universal modular stent graft assembly with a longitudinally offset collateral opening;

Common reference numerals are used throughout the drawings and detailed description to indicate like elements.

DETAILED DESCRIPTION

Figure 4:
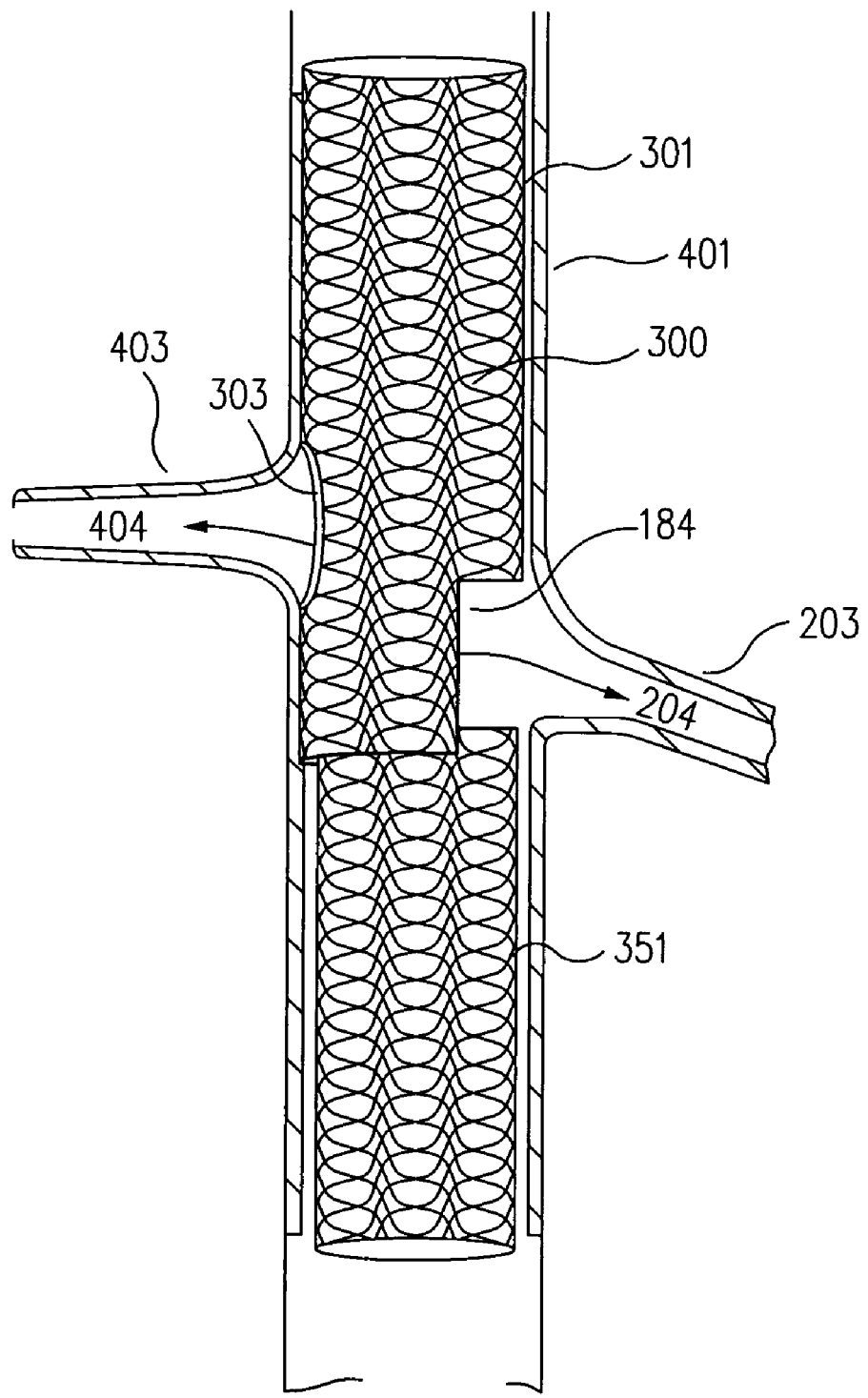
FIG. 4 is a side partial cutaway view of the dual opening universal modular stent graft assembly of FIGS. 3A to 3C deployed in a patient's parent artery.
Figures 5A, 5B:
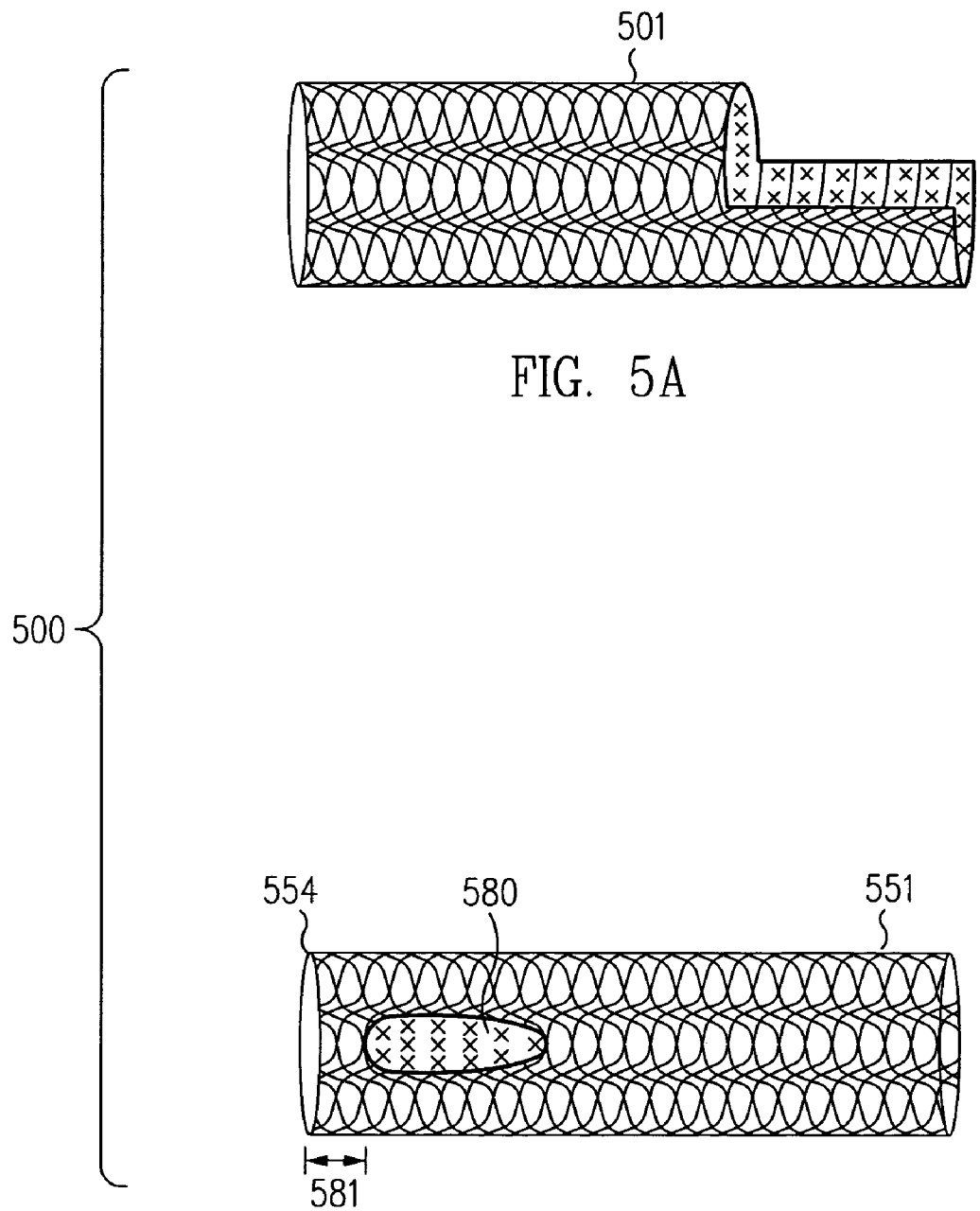
FIG. 5A is a side perspective-like view of a first component of a universal modular stent graft assembly.
FIG. 5B is a side perspective-like view of a second component of a universal modular stent graft assembly.
Figure 6A:
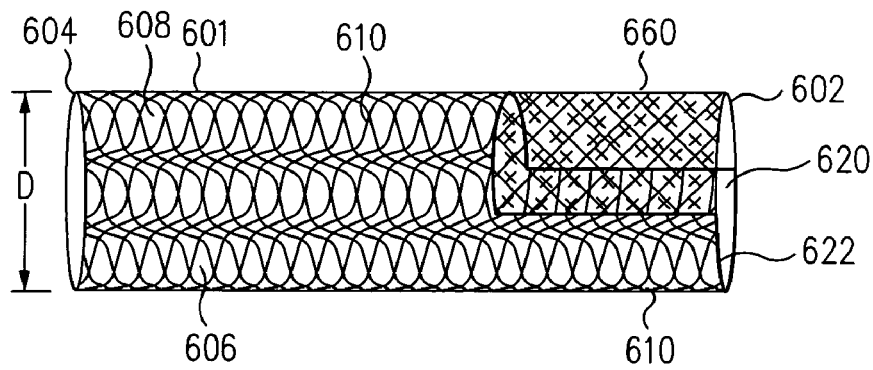
FIG. 6A is a side perspective-like view of a first component of a reinforced universal modular stent graft assembly.
Figure 6B:
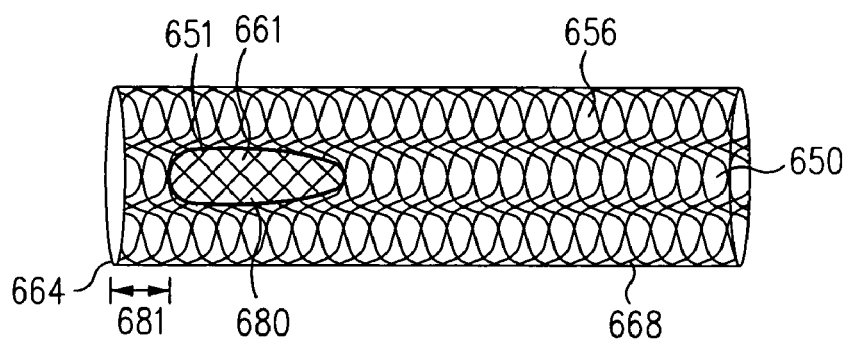
FIG. 6B is a side perspective-like view of a second component of a reinforced universal modular stent graft assembly.
Figure 6C:
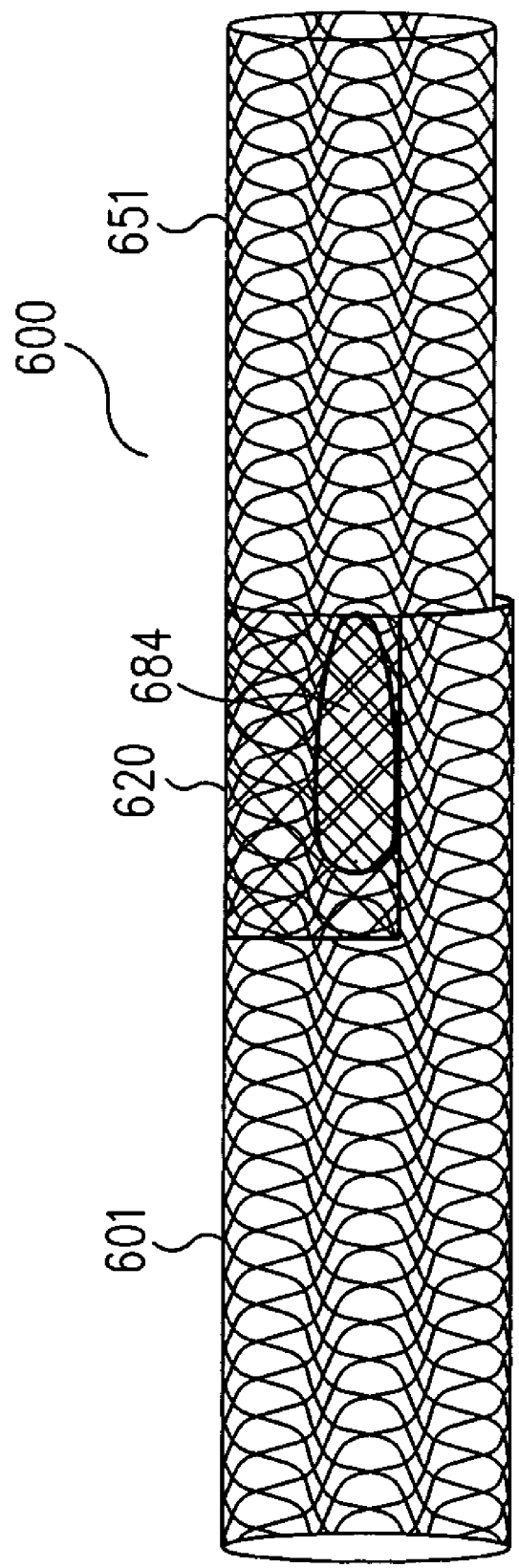
FIG. 6C is a side perspective-like view of the second component of FIG. 6B coupled with the first component of FIG. 6A to form a reinforced universal modular stent graft assembly.

In embodiments in accordance with the principles of the present invention, universal modular stented graft assemblies (100 in FIGS. 1A to 1K and 2A, 2B, 300 in FIGS. 3A to 3C and 4, 500 in FIG. 5A to 5C, 600 in FIGS. 6A to 6C) are assembled (FIGS. 1C to 1I), on site, i.e. at the hospital or in the operating room, and often in a patient's parent artery (201 in FIGS. 2A and 2B, 401 in FIG. 4), from at least two components; a first component (101 in FIGS. 1A to 1K and 2A to 2B, 301 in FIGS. 3A to 3C and 4, 501 in FIG. 5A to 5C, 601 in FIGS. 6A to 6C) and a second component (151 in FIGS. 1A to 1K and 2A to 2B, 351 in FIGS. 3A to 3C and 4, 551 in FIG. 5A to 5C, 651 in FIGS. 6A to 6C). The first and second components each include a window, or fenestration (120 and 180 in FIGS. 1A to 1K and 2A to 2B, 620 and 680 in FIGS. 6A to 6C). In one example, the second component has a diameter (d in FIG. 1B) usually slightly smaller than the diameter (D in FIG. 1A) of the first component so that the second component couples with the first component by fitting at least partially in the first component (FIGS. 1C to 1K) to form the universal modular stent graft assembly.

As the first and second components are assembled, the first and second components are adjusted longitudinally and radially relative to each other so that the first and second component windows overlap to form an adjustable collateral opening (184 in FIGS. 1E to 1I, 2A and 2B, 3C and 4, 584 in FIGS. 5C and 5D, 684 in FIG. 6C) in the universal modular stent graft assembly. By adjusting the relative longitudinal and radial positions of the first and second components during assembly, the universal modular stent graft assembly (FIGS. 1E to 1K), the longitudinal position of the adjustable collateral opening, the length of the adjustable collateral opening, the width of the adjustable collateral opening, and the radial positioning of the adjustable collateral opening can be varied to meet the needs of the particular application.

Figures 1A, 1B:
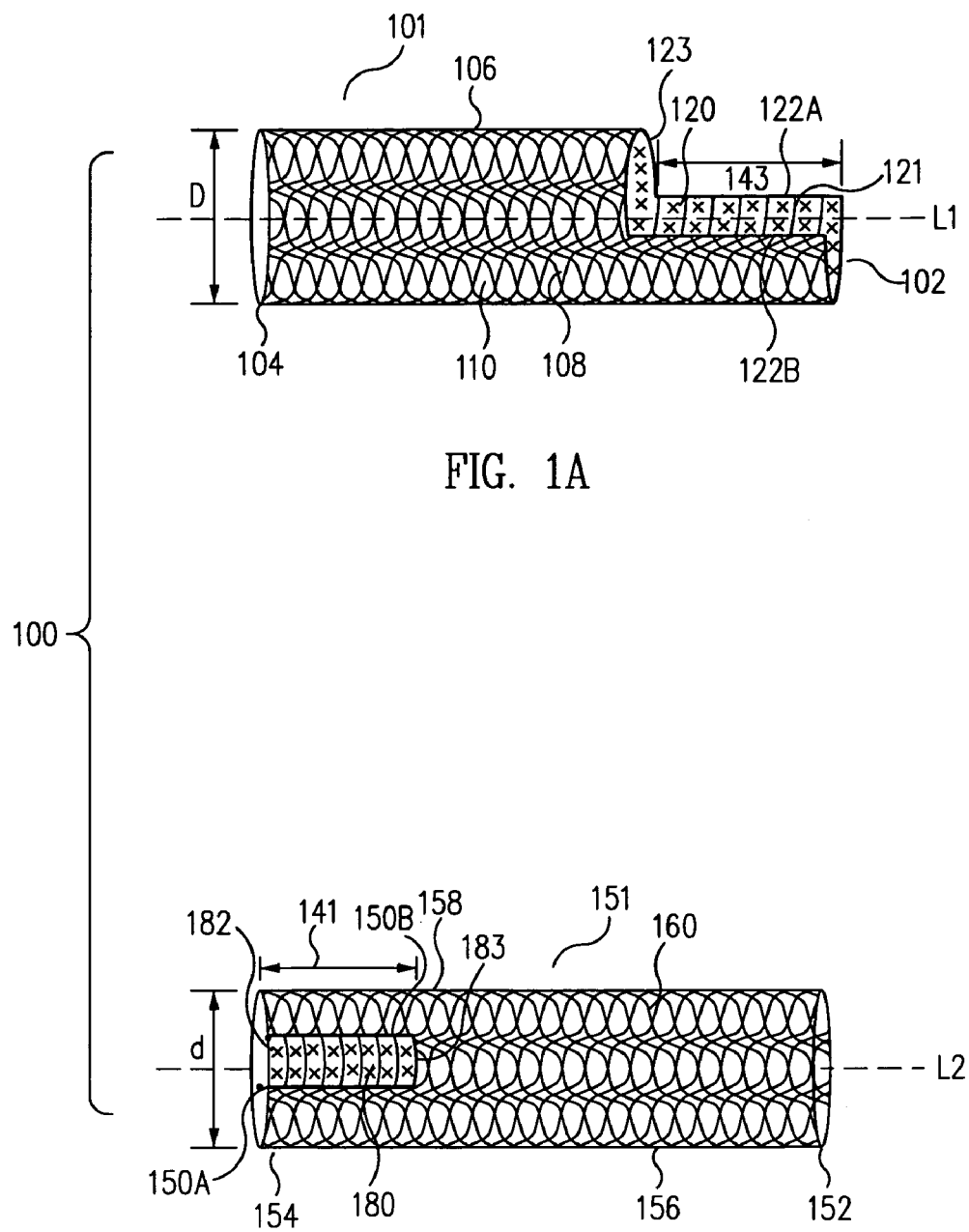
FIG. 1A is a side perspective-like view of a first component of a universal modular stent graft assembly.
FIG. 1B is a side perspective-like view of a second component of a universal modular stent graft assembly.

FIG. 1A and FIG. 1B together show side perspective-like views of the components 101 and 151 of a universal modular stent graft assembly 100 in one embodiment in accordance with the present invention. In particular, FIG. 1A is a perspective-like view of one example of a first component 101 of universal modular stent graft assembly 100 and FIG. 1B is a perspective-like view of one example of a second component 151 of universal modular stent graft assembly 100.

As shown in FIG. 1A, in one example, first component 101 of universal modular stent graft assembly 100 is a substantially circular cylinder and includes a proximal, e.g., first, end 102 and a distal, e.g., second, end 104 connected by a generally circularly cylindrical body 106. Further, as shown in FIG. 1A, first component 101 of universal modular stent graft assembly 100 has a longitudinal axis L1 running through body 106 from proximal end 102 to distal end 104.

In one example, distal end 104 is substantially circularly cylindrical, body 106 is substantially circularly cylindrical and distal end 104 and body 106 have the same diameter D. However, in alternative embodiments, portions (not shown) of a body (e.g., 106) have a diameter greater than or less than the diameter of distal end 104.

In addition, as shown in FIG. 1A, in one example, first component 101 of universal modular stent graft assembly 100 includes a first component window, or fenestration, 120, sometimes called a first component lateral opening 120, extending from the proximal most end of proximal end 102. In one example, first component window 120 is a circular cylindrical cut out portion in body 106 that exposes interior right circular cylinder wall 121. In one embodiment in accordance with the present invention, first component window 120 includes (is defined by) a radial window perimeter 123, sometimes called a radial edge 123 of first component 101, and a longitudinal window perimeter 122A, 122B, sometimes call first and second longitudinal edges 122A, 122B of first component 101. As illustrated in FIG. 1A, radial edge 123 extends between first longitudinal edge 122A and second longitudinal edge 122B. In one example, radial window perimeter 123 has a value of between 25 and 270 degrees and a length of a side length 143 of longitudinal window perimeter 122A, B is between 0.5 inch to 2.0 inches, however, as will readily apparent those of skill in the art from the discussion below, the values of radial window perimeter 123 and longitudinal window perimeter side length 143 of first component window 120 can be any values desired by the manufacturer or the end user of universal modular stent graft assembly 100.

In addition, while first component window 120 is described above, and shown in FIG. 1A, as a substantially rectangular lateral opening with substantially straight longitudinal window perimeter side length 143, those of skill in the art will readily recognize that second component window 120 can be constructed in any shape desired, including but not limited to, circular, oval, square, or diamond.

In addition, those of skill in the art will recognize that, although first component 101 of universal modular stent graft assembly 100 is described above as being generally cylindrical, in an alternative embodiment, first component 101 of universal modular stent graft assembly 100 is eccentric, i.e., non cylindrical.

As shown in FIG. 1A, body 106 of first component 101 of universal modular stent graft assembly 100 includes a stent body mesh 108 made of stainless steel, nitinol, or other similar materials, adapted to render first component 101 of universal modular stent graft assembly 100 flexible and, as well, capable of being reduced in dimension for insertion into various delivery devices such as a catheter or lumen and attendant balloon (not shown). As discussed below, these delivery systems are well known in the art. Moreover, it is also well known in the art to construct stented grafts of various materials such as stainless steel or nitinol, capable of being reduced in size by stress or temperature and, upon delivery to a diseased artery, capable of being reformed to their original size and shape.

In one embodiment in accordance with the present invention, body 106 of first component 101 of universal modular stent graft assembly 100 also includes a graft 110 comprised of a hollow tube of material, such as Dacron, that is typically sewn into position or expanded through the use of a stented balloon catheter (not shown) such that stent body mesh 108 and graft 110 are coupled to form the hollow tubular structure making up body 106.

FIG. 1B shows a side perspective-like view of second component 151 of universal modular stent graft assembly 100. As shown in FIG. 1B, in one example, second component 151 of universal modular stent graft assembly 100 is substantially cylindrical and includes a proximal, e.g., first, end 152, a distal, e.g., second, end 154 connected by a body 156. Further, as shown in FIG. 1B, second component 151 of universal modular stent graft assembly 100 has a longitudinal axis L2 running through body 156 from proximal end 152 to distal end 154.

In one example, proximal end 152 is substantially circularly cylindrical, body 156 is substantially circularly cylindrical and distal end 154 is substantially circularly cylindrical. In one example, proximal end 152, distal end 154 include loop wires (not shown) to provide radial strength to proximal end 152, distal end 154. In one example, proximal end 152, distal end 154, and body 156 have the same diameter d. However, in alternative embodiments, a portion (not shown) of body (e.g., 156) has a diameter greater than or less than the diameter d of distal end (e.g., 154). In one embodiment, diameter d of distal end 154, and body 156 of second component 151 of universal modular stent graft assembly 100, is smaller than diameter D of proximal end 102 of first component 101 of universal modular stent graft assembly 100 (FIG. 1A) such that distal end 154 (FIG. 1B), and at least a portion of body 156 of second component 151 of universal modular stent graft assembly 100 fit within proximal end 102 and at least a portion of body 106 of first component 101 of universal modular stent graft assembly 100 (FIG. 1A).

As with first component 101 of universal modular stent graft assembly 100, although second component 151 of universal modular stent graft assembly 100 (FIG. 1B) is described above as being generally cylindrical, in an alternative embodiment, second component 151 of universal modular stent graft assembly 100 is eccentric, i.e., non cylindrical.

As shown in FIG. 1B, in one example, body 156 of second component 151 of universal modular stent graft assembly 100 includes a stent body mesh 158 made of stainless steel, nitinol, or other similar materials, adapted to render second component 151 of universal modular stent graft assembly 100 flexible and, as well, capable of being reduced in dimension for insertion into various delivery devices such as a catheter or lumen and attendant balloon (not shown). As discussed below, these delivery systems are well known in the art. Moreover, it is also well known in the art to construct stented grafts of various materials such as stainless steel or nitinol, capable of being reduced in size by stress or temperature and, upon delivery to a diseased artery, capable of being reformed to their original size and shape.

In one example, body 156 of second component 151 of universal modular stent graft assembly 100 also includes a graft 160 comprised of a hollow tube of material, such as Dacron, that is typically sewn into position or expanded through the use of a stented balloon catheter (not shown) such that stent body mesh 158 and graft 160 are coupled to form the hollow tubular structure of body 156.

As shown in FIG. 1B, second component 151 of universal modular stent graft assembly 100 also includes a second component window, or fenestration, 180, sometimes called a second component lateral opening 180, extending from the distal most end 154. In one example, second component window 180 is a circular cylindrical cut out portion in body 156 that exposes interior left circular cylinder wall 182. In one embodiment in accordance with the present invention, second component window 180 includes (is defined by) a radial window perimeter 183, sometimes called a radial edge 183 of second component 151, and a longitudinal window perimeter 150A, 150B, sometimes call first and second longitudinal edges 150A, 150B of second component 151. As illustrated in FIG. 1B, radial edge 183 extendes between first longitudinal edge 150A and second longitudinal edge 150B. In one example radial window perimeter 183 has a value of between 270 and 25 degrees and longitudinal window perimeter 150A, B has a side length 141 between 0.5 inch to 3.0 inches, however, as will readily apparent those of skill in the art from the discussion below, the values of radial window perimeter 183 and longitudinal window perimeter side length 141 of second component window 180 can be any values desired by the manufacturer or the end user of universal modular stent graft assembly 100.

In addition, while second component window 180 is described above, and shown in FIG. 1B, as a substantially rectangular lateral opening with substantially straight longitudinal window perimeter side length 141, those of skill in the art will readily recognize that second component window 180 can be constructed in any shape desired, including but not limited to, circular, oval, square, or diamond and can include a loop wire to provide additional strength.

As discussed above, in one example, proximal end 152, distal end 154, and body 156 of second component 151 of universal modular stent graft assembly 100 have the same diameter d, and diameter d is smaller than diameter D of proximal end 102, distal end 104, and body 106 of first component 101 of universal modular stent graft assembly 100 (FIG. 1A). Consequently, as shown in FIGS. 1C to 1K distal end 154 and at least a portion of body 156 of second component 151 of universal modular stent graft assembly 100 (FIG. 1B) fits within, or couples with, proximal end 102 and at least a portion of body 106 of first component 101 of universal modular stent graft assembly 100 (FIG. 1A).

Figure 1C:
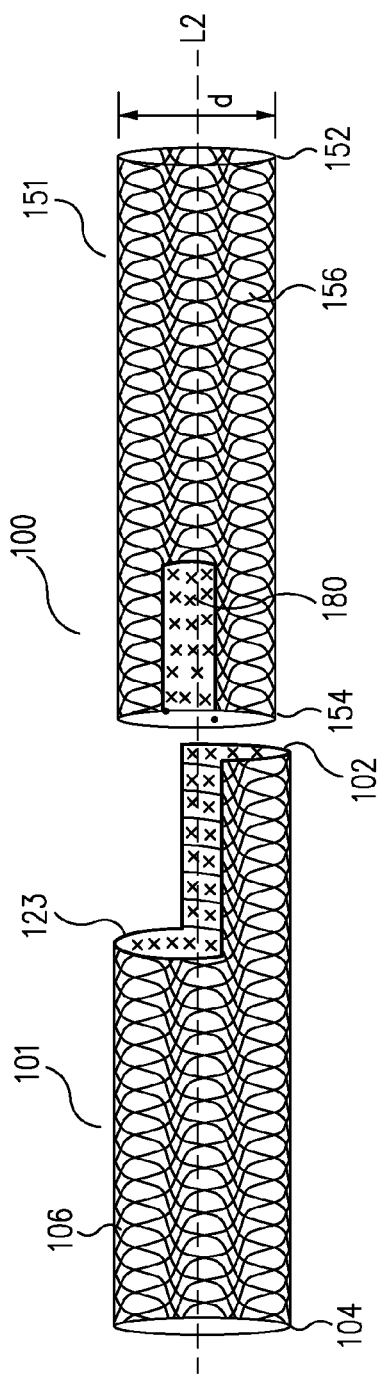
FIG. 1C is a side perspective-like view of the second component of FIG. 1B placed in alignment with the first component of FIG. 1A, prior to the coupling of the second component of FIG. 1B with the first component of FIG. 1A.

As shown in FIG. 1C, in one example, second component 151 is placed in alignment with first component 101 of universal modular stent graft assembly 100 such that distal end 154 of second component 151 of universal modular stent graft assembly 100 faces proximal end 102 of first component 101 of universal modular stent graft assembly 100 and longitudinal axis L1 of first component 101 of universal modular stent graft assembly 100 is generally aligned with longitudinal axis L2 of second component 151 of universal modular stent graft assembly 100 to form co-axis L2/L1.

Figure 1D:
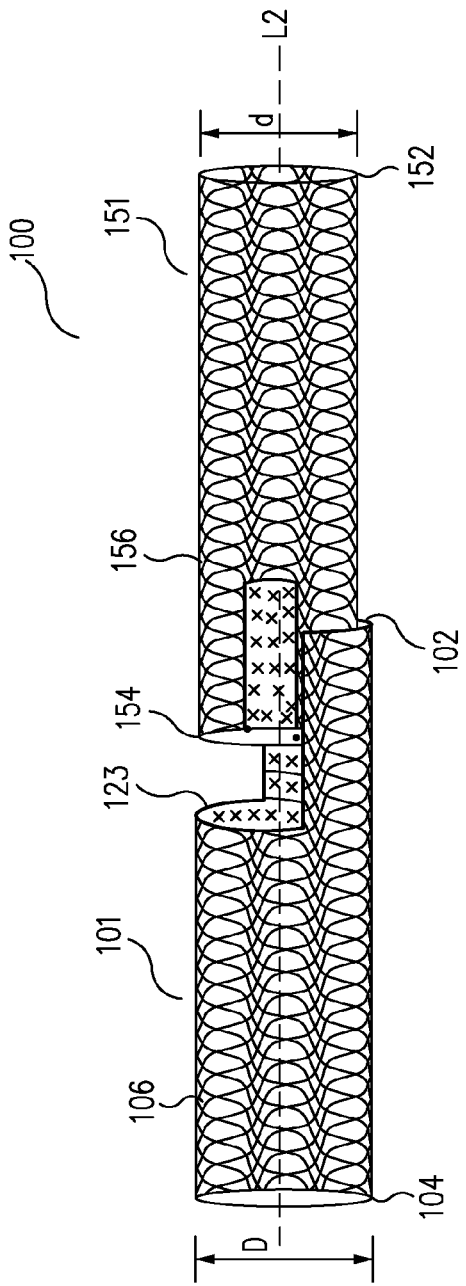
FIG. 1D is a side perspective-like view of the second component of FIG. 1B being coupled with the first component of FIG. 1A.

As shown in FIG. 1D, second component 151 is coupled with first component 101 to form universal modular stent graft assembly 100 by placing distal end 154 of second component 151 of universal modular stent graft assembly 100 inside proximal end 102 of first component 101 of universal modular stent graft assembly 100.Cylindrical universal modular stent graft assembly 100 includes a proximal end defined by proximal end 152 of second component 151 and a distal end defined by distal end 104 of first component 101.

As shown in FIG. 1E, when second component 151 of universal modular stent graft assembly 100 is coupled with first component 101 of universal modular stent graft assembly 100, distal end 154, and at least a portion 188 of body 156 of second component 151 of universal modular stent graft assembly 100, is positioned within proximal end 102 and body 106 of first component 101 of universal modular stent graft assembly 100. The coupling of second component 151 of universal modular stent graft assembly 100 with first component 101 of universal modular stent graft assembly 100 results in an adjustable collateral fenestration, or opening, 184 in universal modular stent graft assembly 100 offset from and in between proximal end 152 and distal end 104 of universal modular stent graft assembly 100. More particularly, an overlap of second component lateral opening 180 (see FIG. 1B) and first component lateral opening 120 (see FIG. 1A) form a single collateral opening 184 in universal modular stent graft assembly 100 as shown in FIG.1E. Second component body 156 covers first component lateral opening 120 except at collateral opening 184. Similarly, first component body 106 covers second component lateral opening 180 except at collateral opening 184.

As seen in FIGS. 1E and 1F, in one embodiment in accordance with the present invention, a longitudinal dimension, or length, 187 of adjustable collateral opening 184 in universal modular stent graft assembly 100, and the longitudinal positioning of adjustable collateral opening 184, is variable and can be adjusted by increasing or decreasing the portion 188 (FIG. 1E)/198 (FIG. 1F) of body 156 of second component 151 of universal modular stent graft assembly 100 that is positioned within proximal end 102 and body 106 of first component 101 of universal modular stent graft assembly 100. In one example, radiopaque markers (not shown) are used to position second component 151 of universal modular stent graft assembly 100 within proximal end 102 and body 106 of first component 101 of universal modular stent graft assembly 100 by methods well known to those of skill in the art. Consequently, length 187 (FIG. 1E) of adjustable collateral opening 184 can be decreased to length 197 (FIG. 1F) prior to deployment by pushing second component 151 of universal modular stent graft assembly 100 in the direction shown by arrow 190, and further into first component 101 of universal modular stent graft assembly 100, thereby increasing the portion 188 (FIG. 1E) of body 156 of second component 151 of universal modular stent graft assembly 100 to portion 198 (FIG. 1F) that is positioned within proximal end 102 and body 106 of first component 101 of universal modular stent graft assembly 100.

Likewise, length 197 (FIG. 1F) of adjustable collateral opening 184 can be increased prior to deployment by pulling second component 151 of universal modular stent graft assembly 100 in the direction shown by arrow 191, and further out of first component 101 of universal modular stent graft assembly 100, thereby decreasing portion 198 of body 156 of second component 151 of universal modular stent graft assembly 100 to portion 188 (FIG. 1E) that is positioned within proximal end 102 and body 106 of first component 101 of universal modular stent graft assembly 100.

In addition to providing for adjustment of the longitudinal dimension, or length, 187 (FIG. 1E)/197 (FIG. 1F), and the longitudinal positioning, of adjustable collateral opening 184 in universal modular stent graft assembly 100 as discussed above, as seen in FIG. 1G and FIG. 1H, a radial dimension, or width, 189 (FIG. 1G)/199 (FIG. 1H), and the radial positioning (FIG. 1I), of adjustable collateral opening 184 in universal modular stent graft assembly 100 is also variable.

As shown in FIGS. 1G and 1H, width 189 (FIG. 1G) of adjustable collateral opening 184 can be decreased to width 199 (FIG. 1H) by rotating second component 151 of universal modular stent graft assembly 100 in the direction shown by arrow 164 about common radial axis L2/L1 of universal modular stent graft assembly 100. Likewise, as shown in FIG. 1G, width 199 (FIG. 1H) of adjustable collateral opening 184 can be increased to width 189 (FIG. 1G) by rotating second component 151 of universal modular stent graft assembly 100 in the direction shown by arrow 162 about common radial axis L2/L1 of universal modular stent graft assembly 100.

Figure 1I:
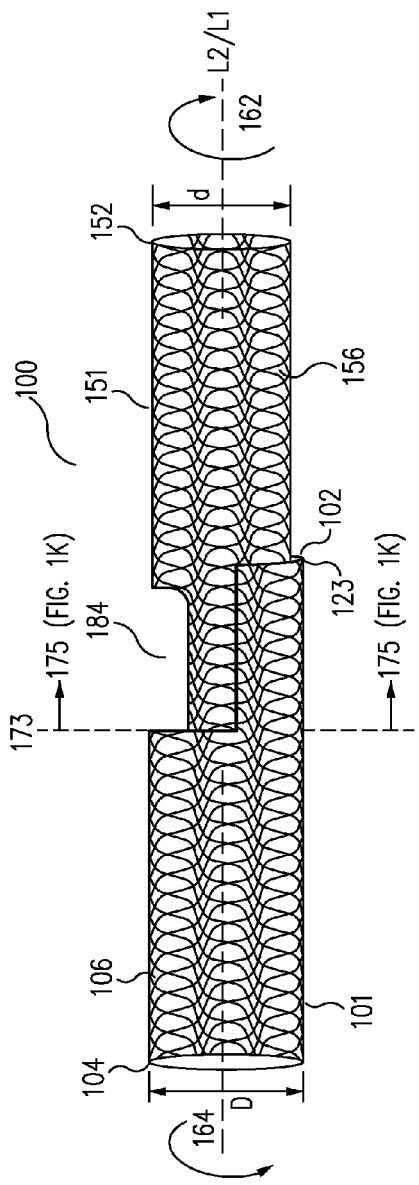
FIG. 1I is a side perspective-like view of the second component of FIG. 1B coupled with the first component of FIG. 1A to form a universal modular stent graft assembly, the universal modular stent graft assembly having been adjusted around its longitudinal axis to have an opening of a first width and at a second radial position.
Figure 1J:
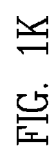
FIG. 1J is a cross-sectional view of the second component of FIG. 1A coupled with the first component of FIG. 1B to form the universal modular stent graft assembly of FIG. 1G as seen at the section cut at 170 in FIG. 1G when viewed in direction 171 in FIG. 1G.
Figure 1K:
FIG. 1K is a cross-sectional view of the second component of FIG. 1A coupled with the first component of FIG. 1B to form the universal modular stent graft assembly of FIG. 1I as seen at the section cut at 173 in FIG. 1I when viewed in direction 175 in FIG. 1I.

In addition, as shown in FIG. 1G, FIG. 1I, FIG. 1J, and FIG. 1K, the radial position of adjustable collateral opening 184 can be adjusted by rotating second component 151 of universal modular stent graft assembly 100 in either the direction shown by arrows 162 or 164 about common radial axis L2/L1 when viewed in direction 171 in FIGS. 1G and 173 in FIG. 1I. FIG. 1J is a cross-sectional view of second component 151 coupled with first component 101 as seen along line 170 in FIG. 1G when viewed in direction 171. FIG. 1K is a cross-sectional view of second component 151 coupled with first component 101 as seen along line 173 in FIG. 1I when viewed in direction 175. Comparing FIG. 1G and FIG. 1J with FIG. 1I and FIG. 1K, second component 151 of universal modular stent graft assembly 100 is rotated about common radial axis L2/L1 in the direction shown by arrow 162 such that the radial position 177 of adjustable collateral opening 184 in FIG. 1G/FIG. 1J is moved in the direction of arrow 162 to position 179 in FIG. 1I/FIG. 1K.

In the discussion above, the radial position of adjustable collateral opening 184 was adjusted by rotating second component 151 of universal modular stent graft assembly 100 in either the direction shown by arrows 162 or 164 about common radial axis L2/L1. Of course, those of skill in the art will readily recognize that the radial position of adjustable collateral opening 184 can also be adjusted by rotating first component 101 of universal modular stent graft assembly 100 in either the direction shown by arrows 164 or 162 about common radial axis L2/L1 as well.

As shown above, universal modular stent graft assembly 100, in contrast to the prior art structures and methods, provides for variable positioning 177 (FIG. 1J)/179 (FIG. 1K) of adjustable collateral opening 184 and variable length 187 (FIG. 1E)/197 (FIG. 1F) and width 189 (FIG. 1E)/199 (FIG. 1F). Consequently, universal modular stent graft assembly 100 does not need to be custom made and universal modular stent graft assembly 100 can be assembled from first component 101 and second component 151 on site, and even during deployment in the artery, and then the position, length and width of adjustable collateral opening 184 can be modified to provide adjustable collateral opening 184 at the exact location needed, and general dimensions needed, to meet the particular needs of the patient, and the artery structure, being repaired.

Figure 2A:
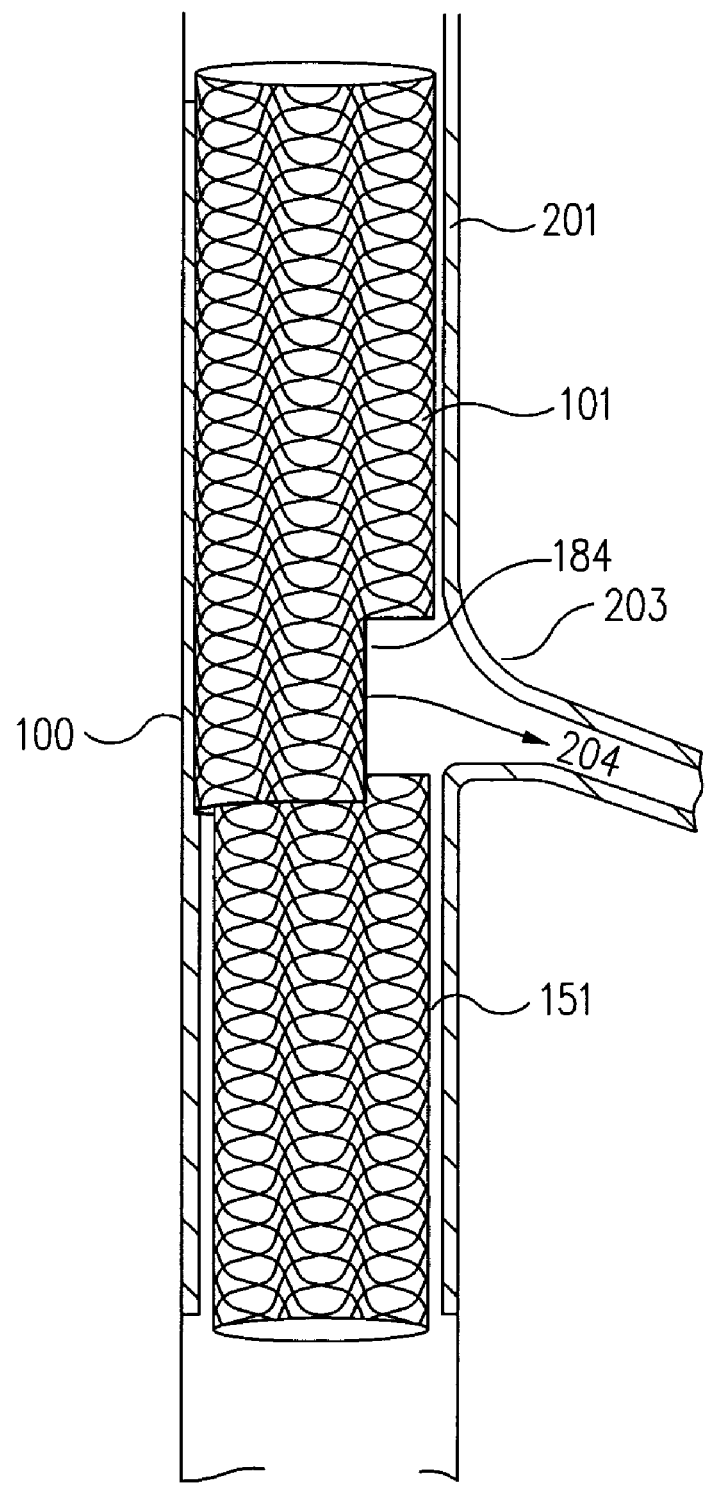
FIG. 2A is a side partial cutaway view of the universal modular stent graft assembly of FIGS. 1A to 1I deployed in a patient's parent artery.

FIG. 2A is a side cutaway view of the universal modular stent graft assembly 100 of FIGS. 1A to 1K deployed in a patient's parent artery 201 with adjustable collateral opening 184 positioned and adjusted to provide blood flow to the patient's collateral artery 203 in the direction shown by arrow 204.

Universal modular stent graft assembly 100 can be deployed by standard methods well known to those of skill in the art. For instance, in one example, first component 101 of universal modular stent graft assembly 100 is deployed first, either as a self-expanding structure or by balloon catheter, by methods well known to those of skill in the art. In one example, first component 101 of universal modular stent graft assembly 100 is at first only partially deployed by methods well known to those of skill in the art, such as only partially pulling back a deployment sheath (not shown), and then first component 101 of universal modular stent graft assembly 100 is rotated into the desired position. In this example, once first component 101 of universal modular stent graft assembly 100 is positioned as desired, first component 101 of universal modular stent graft assembly 100 is fully deployed by fully removing the deployment sheath (not shown).

In one example, once first component 101 of universal modular stent graft assembly 100 is fully positioned and deployed as described above by methods well known to those of skill in the art, second component 151 of universal modular stent graft assembly 100 is also deployed by methods well known to those of skill in the art, either as a self-expanding structure or by balloon catheter. In one example, second component 151 of universal modular stent graft assembly 100, like first component 101 of universal modular stent graft assembly 100, is at first only partially deployed by methods well known to those of skill in the art, such as by partially pulling back a deployment sheath (not shown), and then second component 151 of universal modular stent graft assembly 100 is also rotated to provide adjustable collateral opening 184 with the desired position and dimensions as discussed above with respect to FIGS. 1E to 1K.

In one example, radiopaque markers (not shown) on second component 151 of universal modular stent graft assembly 100 are used by methods well known to those of skill in the art to position second component 151 of universal modular stent graft assembly 100. In one example, once second component 151 of universal modular stent graft assembly 100 is positioned within proximal end 102 and body 106 of first component 101 of universal modular stent graft assembly 100 as desired, second component 151 of universal modular stent graft assembly 100 is fully deployed by methods well known to those of skill in the art, such as by completely pulling back a deployment sheath (not shown). In one example, once second component 151 of universal modular stent graft assembly 100 is fully deployed, second component 151 of universal modular stent graft assembly 100 and first component 101 of universal modular stent graft assembly 100 are held in position by a frictional fit or inter-engagement. In this example, second component 151 of universal modular stent graft assembly 100 and first component 101 of universal modular stent graft assembly 100 are sized, i.e., the diameters D and d in FIGS. 1A and 1B are chosen, such that, once fully deployed and assembled into universal modular stent graft assembly 100 interaction between second component 151 of universal modular stent graft assembly 100 and first component 101 of universal modular stent graft assembly 100 creates a frictional force through their radial interference.

In some instances, it may be necessary to provide additional support to collateral artery 203 and to further promote the flow of blood from adjustable collateral opening 184 into collateral artery 203. In these instances, a collateral stented graft structure can be used with universal modular stent graft assembly 100.

Figure 2B:
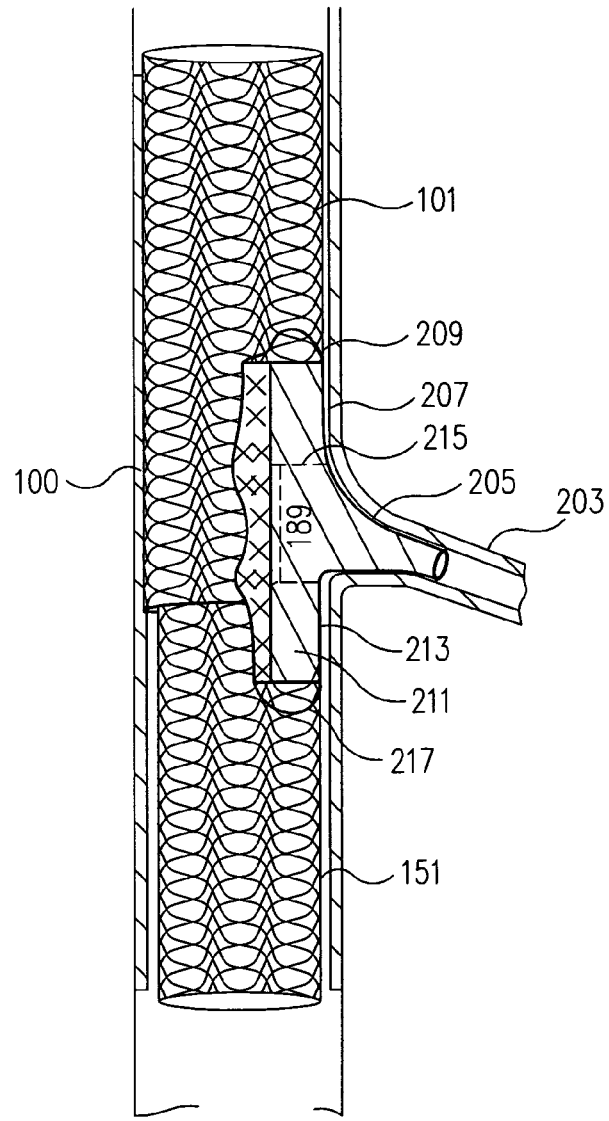
FIG. 2B shows a side partial cutaway view of the universal modular stent graft assembly of FIG. 2A and a collateral stented graft structure deployed in a patient's collateral artery.

FIG. 2B shows a side view of universal modular stent graft assembly 100 deployed as shown in FIG. 2A and including a collateral stent graft structure 205 deployed in collateral artery 203 in one embodiment in accordance with the present invention. In FIG. 2B, a portion of universal modular stent graft assembly 100 is shown partial cutaway along line 217 to expose the collateral stent graft structure 205 for illustrative purposes.

Figure 2C:
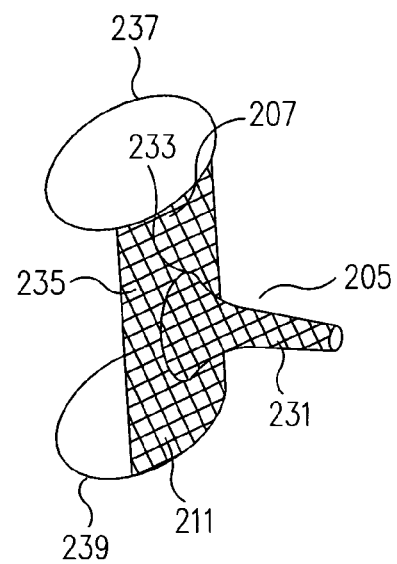
FIG. 2C shows a perspective-like view of a typically collateral stent graft structure of FIG. 2B including a base, with first base portion and second base portion, and a collateral extension.

FIG. 2C shows a perspective-like view of a typically collateral stent graft structure 205 including a base 235, with first base portion 207 and second base portion 211, a collateral extension 231, and anchor rings 237 and 239. In one example, collateral stent graft structure 205 includes a stent body mesh 233 made of stainless steel, nitinol, or other similar materials, and a graft 235 comprised of a hollow tube of material, such as Dacron. Reinforcing rings, or anchor rings, 237 and 239 provide anchoring for collateral stent graft structure 205 in universal modular stent graft assembly 100.

Collateral stent graft structure 205 is typically deployed by passing a guide wire (not shown) through the vasculature and into adjustable collateral opening 184 of universal modular stent graft assembly 100. Collateral stent graft structure 205 is then guided to the location of adjustable collateral opening 184 by the guide wire (not shown). Collateral stent graft structure 205 is then deployed to substantially seal adjustable collateral opening 184. The cylindrical-like structure formed by base 235, with first base portion 207 and second base portion 211, and anchor rings 237 and 239 then expands inside the body of universal modular stent graft assembly 100 to anchor collateral stent graft structure 205 in place.

In one example, collateral stent graft structure 205 is deployed, after first component 101 and second component 151 of universal modular stent graft assembly 100 are fully positioned and deployed as described above. As discussed above, in one example, first base portion 207 of collateral stent graft structure 205 is coupled with wall portion 209 of first component of universal modular stent graft assembly 100 and second base portion 211 of collateral stent graft structure 205 is coupled to wall portion 213 of second component of universal modular stent graft assembly 100, thereby forming a seal around perimeter 215 of adjustable collateral opening 184 of universal modular stent graft assembly 100. Consequently, in this example, the combination of universal modular stent graft assembly 100 and collateral stent graft structure 205 provides additional support to collateral artery 203 and further promotes the flow of blood from adjustable collateral opening 184 into collateral artery 203.

Universal modular stent graft assemblies, such as universal modular stent graft assembly 100, can also be used with/as other types of stent grafts. In one example (not shown), universal modular stent graft assemblies, such as universal modular stent graft assembly 100, can be used with bifurcated stent grafts (not shown), where the completed stent graft assembly creates a "Y" structure to cross a bifurcation, or as Aorto Uni-Iliac (AUI) stent grafts (not shown), where the graft is a tapered tube larger at one end, such as distal end 104 or proximal end 102 in FIG. 1A, and tapering down to the other end, such as proximal end 102 or distal end 104 in FIG. 1A.

In some instances, a bifurcated stent graft assembly (not shown) cannot be used to cross the bifurcation. In this case, a single tube (not shown) is used to exclude the aneurysm and to provide a flow conduit from the descending aorta (not shown) into one iliac artery (not shown). In this case, the other iliac artery (not shown) is occluded, using an occluder (not shown), and a bypass is created by tying the one good iliac artery (not shown) together with the other side's iliac artery (not shown). In another example (not shown), an Aorto Uni-Iliac (AUI) stent graft assembly can be designed to have a window, similar to window 120 or window 180 in FIGS. 1A and 1B, to form an adjustable collateral opening, such as adjustable collateral opening 184 in FIG. 1E.

As discussed above, the axial dimension, or length, 187/197 of adjustable collateral opening 184 of universal modular stent graft assembly 100 is adjustable (FIGS. 1E and 1F) and the longitudinal positioning of adjustable collateral opening 184 is adjustable (FIGS. 1E and 1F). Likewise, the radial dimension, or width, 189/199 is adjustable (FIGS. 1G and 1H) and the radial positioning of adjustable collateral opening 184 is adjustable (FIGS. 1J and 1K) in universal modular stent graft assembly 100. Consequently, as discussed above, and in contrast to prior art methods and structures, universal modular stent graft assembly 100 does not need to be custom made for each patient. Therefore, universal modular stent graft assembly 100 can be mass-produced with minimal labor costs and kept in inventory on site.

In addition, using universal modular stent graft assembly 100, it not necessary to obtain the exact measurements that were required to build the custom stented graft structures used with prior art techniques such as Taheri '824. Consequently, there is less opportunity to introduce human error in both the measurement taking process and the implementing of those measurements during production/assembly.

In addition, in contrast to the prior art, using universal modular stent graft assembly 100, there is no time lag since the structure is assembled on site by coupling second component 151 of universal modular stent graft assembly 100 with first component 101 of universal modular stent graft assembly 100 to form an adjustable collateral opening 184 in universal modular stent graft assembly 100 and then adjusting the axial dimension, or length, 187/197 of adjustable collateral opening 184, the axial positioning of adjustable collateral opening 184, the radial dimension, or width, 189/199, and the radial positioning of adjustable collateral opening 184 as needed.

In short, universal modular stent graft assembly 100 is less expensive, requires less precise measurement and production techniques, can be kept in inventory on site and can be deployed faster, easier, and in a greater variety of circumstances, than prior art structures and methods. This gives universal modular stent graft assembly 100 a significant advantage over the prior art.

Figure 3A:
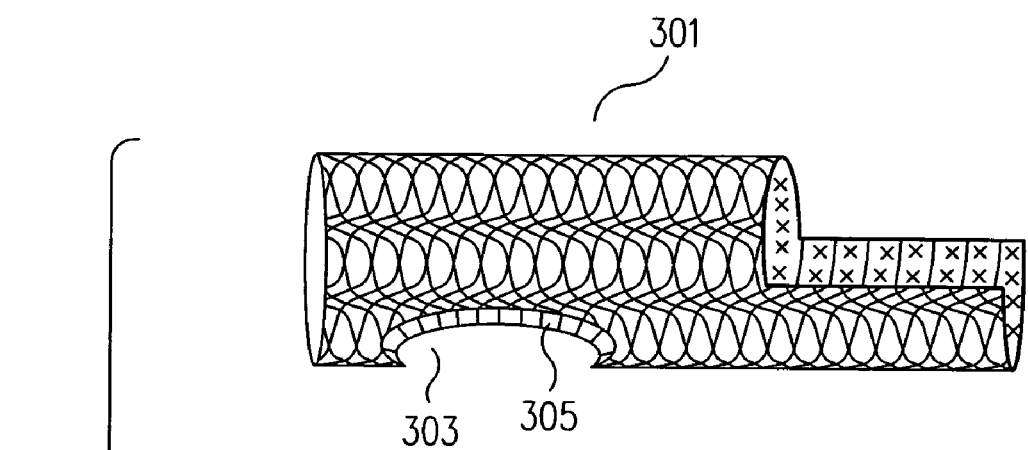
FIG. 3A is a side perspective-like view of a first component of a dual opening universal modular stent graft assembly.

FIG. 3A is a side perspective-like view of a first component 301 of a dual opening universal modular stent graft assembly 300 in one embodiment in accordance with the present invention. As shown in FIG. 3A, first component 301 of a dual opening universal modular stent graft assembly 300 is substantially similar to first component 101 of universal modular stent graft assembly 100 discussed above with respect to FIG. 1A and includes all of the features discussed above with respect to first component 101 of universal modular stent graft assembly 100. Therefore, the description above with respect to first component 101 of universal modular stent graft assembly 100 and FIG. 1A is incorporated by reference here to first component 301 of a dual opening universal modular stent graft assembly 300. However, returning to FIG. 3A, first component 301 of dual opening universal modular stent graft assembly 300 includes fixed collateral fenestration, or opening, 303.

In one example, fixed collateral opening 303 is a substantially circular lateral opening supported and defined by a lateral support collar 305. Lateral support collar 305 can be constructed of a variety of materials, such as plastic or steel and serves to support and define fixed collateral opening 303. Those of skill in the art will readily recognize that while fixed collateral opening 303 is described above as a substantially circular lateral opening, fixed collateral opening 303 can be constructed in any shape desired, including but not limited to, oval, square, diamond or asymmetric.

Figure 3B:
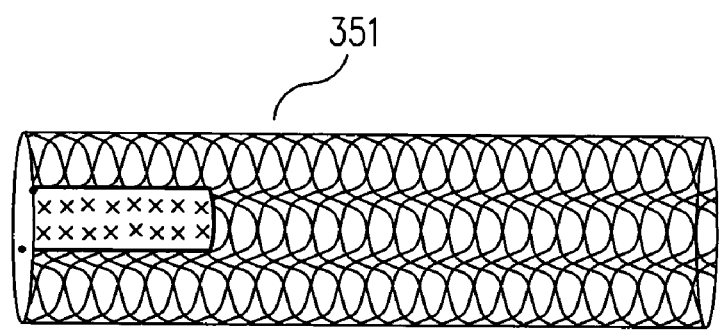
FIG. 3B is a side perspective-like view of a second component of a dual opening universal modular stent graft assembly.

FIG. 3B is a side perspective-like view of a second component 351 of a dual opening universal modular stent graft assembly 300 in one embodiment in accordance with the present invention. As shown in FIG. 3B, second component 351 of a dual opening universal modular stent graft assembly 300 is substantially similar to second component 151 of universal modular stent graft assembly 100 discussed above with respect to FIG. 1B and includes all of the features discussed above with respect to second component 151 of universal modular stent graft assembly 100. Therefore, the description above with respect to second component 151 of universal modular stent graft assembly 100 and FIG. 1B is incorporated by reference here to second component 351 of a dual opening universal modular stent graft assembly 300.

Figure 3C:
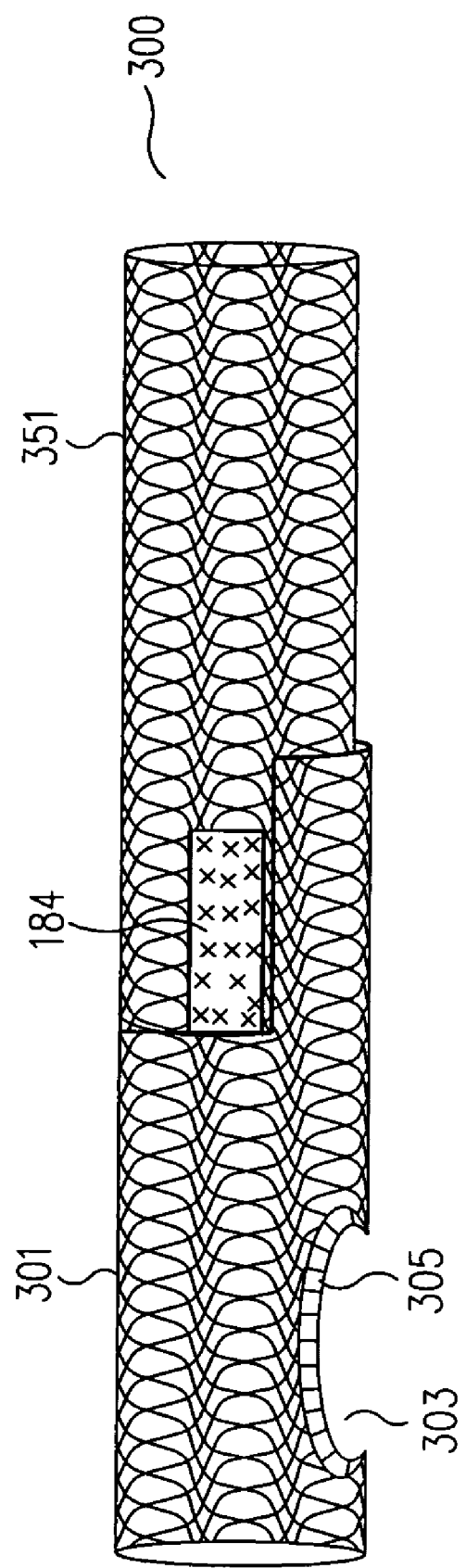
FIG. 3C is a side perspective-like view of the second component of FIG. 3B coupled with the first component of FIG. 3A to form a dual opening universal modular stent graft assembly.

FIG. 3C is a side perspective-like view of second component 351 of FIG. 3B coupled with first component 301 of FIG. 3A to form dual opening universal modular stent graft assembly 300. As shown in FIG. 3C, dual opening universal modular stent graft assembly 300 is substantially similar to universal modular stent graft assembly 100 discussed above with respect to FIGS. 1E to 1K and includes all of the features discussed above with respect to universal modular stent graft assembly 100. Therefore, the description above with respect to universal modular stent graft assembly 100 and FIGS. 1A to 1K is incorporated by reference here to dual opening universal modular stent graft assembly 300. However, returning to FIG. 3C, as discussed above, first component 301 of dual opening universal modular stent graft assembly 300 includes fixed collateral fenestration, or opening, 303 in addition to an adjustable collateral opening 184.

The addition of fixed collateral opening 303 to dual opening universal modular stent graft assembly 300 provides dual opening universal modular stent graft assembly 300 with the capability of allowing blood flow to two collateral arteries. This is a particularly useful capability when treating disease at the intersection of various major arteries, e.g., the aorta and renal arteries or brachycephalic arteries.

Using dual opening universal modular stent graft assembly 300, fixed collateral opening 303 is positioned at a first collateral artery and then adjustable collateral opening 184 is positioned and adjusted as described above with respect to universal modular stent graft assembly 100 and FIGS. 1A to 2B. FIG. 4 is a side cutaway view of dual opening universal modular stent graft assembly 300 of FIGS. 3A to 3C deployed in a patient's parent artery 401 with adjustable collateral opening 184 positioned and adjusted to provide blood flow to patient's collateral artery 203 in the direction shown by arrow 204, as discussed above with respect to FIG. 2A, and fixed collateral opening 303 positioned to provide blood flow to a patient's collateral artery 403 in the direction shown by arrow 404.

As with universal modular stent graft assembly 100, dual opening universal modular stent graft assembly 300 can be deployed by standard methods well known to those of skill in the art. For instance, in one example, first component 301 of dual opening universal modular stent graft assembly 300 is deployed first, either as a self-expanding structure or by balloon catheter, by methods well known to those of skill in the art. In one example, first component 301 of dual opening universal modular stent graft assembly 300 is at first only partially deployed by methods well known to those of skill in the art, such as only partially pulling back a deployment sheath (not shown). In this example, first component 301 of dual opening universal modular stent graft assembly 300 is positioned such that fixed collateral opening 303 is aligned with collateral artery 403 to provide blood flow to collateral artery 403 in the direction shown by arrow 404.

In this example, once first component 301 of dual opening universal modular stent graft assembly 300 is positioned as desired, first component 301 of dual opening universal modular stent graft assembly 300 is fully deployed by fully removing the deployment sheath (not shown).

In one example, once first component 301 of dual opening universal modular stent graft assembly 300 is fully positioned and deployed as described above, by methods well known to those of skill in the art, second component 351 of dual opening universal modular stent graft assembly 300 is also deployed by methods well known to those of skill in the art, either as a self-expanding structure or by balloon catheter. In one example, second component 351 of dual opening universal modular stent graft assembly 300, like first component 301 of dual opening universal modular stent graft assembly 300, is at first only partially deployed by methods well known to those of skill in the art, such as by partially pulling back a deployment sheath (not shown), and then second component 351 of dual opening universal modular stent graft assembly 300 is rotated to provide adjustable collateral opening 184 with the desired position and dimensions as discussed above with respect to FIGS. 1E to 1I.

In one example, radiopaque markers (not shown) on second component 351 of dual opening universal modular stent graft assembly 300 are used by methods well known to those of skill in the art to position second component 351 of dual opening universal modular stent graft assembly 300. In one example, once second component 351 of dual opening universal modular stent graft assembly 300 is positioned within first component 301 of dual opening universal modular stent graft assembly 300 as desired, second component 351 of dual opening universal modular stent graft assembly 300 is fully deployed by methods well known to those of skill in the art, such as by completely pulling back a deployment sheath (not shown). In one example, once second component 351 of dual opening universal modular stent graft assembly 300 is fully deployed, second component 351 of dual opening universal modular stent graft assembly 300 and first component 301 of dual opening universal modular stent graft assembly 300 are held in position by a frictional fit or inter-engagement. In this example, second component 351 of dual opening universal modular stent graft assembly 300 and first component 301 of dual opening universal modular stent graft assembly 300 are sized such that, once fully deployed and assembled into dual opening universal modular stent graft assembly 300 interaction between second component 351 of dual opening universal modular stent graft assembly 300 and first component 301 of dual opening universal modular stent graft assembly 300 creates a frictional force through their radial interference.

As discussed above with respect to FIG. 2B, in some instances, it may be necessary to provide additional support to collateral artery 203 and collateral artery 403 in FIG. 4 to further promote the flow of blood from adjustable collateral opening 184 and into collateral artery 203 and/or from fixed collateral opening 303 to collateral artery 403. In these instances, collateral stented graft structures (not shown), similar to collateral stent graft structure 205 discussed above with respect to FIG. 2B, can be used with dual opening universal modular stent graft assembly 300. The structure of any such collateral stented graft structures, and the procedure for deploying any such collateral stented graft structures, are well known to those of skill in the art and would be substantially similar to the procedure discussed above with respect to collateral stent graft structure 205 and FIG. 2B. Therefore, the reader is referred to the discussion above and a detailed description is omitted herein to avoid detracting from the present invention.

FIG. 5A is a side perspective-like view of a first component 501 of a universal modular stent graft assembly 500 in one embodiment in accordance with the present invention. As shown in FIG. 5A, first component 501 of universal modular stent graft assembly 500 is substantially similar to first component 101 of universal modular stent graft assembly 100 discussed above with respect to FIG. 1A and includes all of the features discussed above with respect to first component 101 of universal modular stent graft assembly 100. Therefore, the description above with respect to first component 101 of universal modular stent graft assembly 100 and FIG.1A is incorporated by reference here to first component 501 of universal modular stent graft assembly 500.

FIG. 5B is a side perspective-like view of a second component 551 of universal modular stent graft assembly 500 in one embodiment in accordance with the present invention. As shown in FIG. 5B, second component 551 of universal modular stent graft assembly 500 is substantially similar to second component 151 of universal modular stent graft assembly 100 discussed above with respect to FIG. 1B and includes substantially all of the features discussed above with respect second component 151 of universal modular stent graft assembly 100. Therefore, the description above with respect to second component 151 of universal modular stent graft assembly 100 and FIG. 1B is incorporated by reference here to second component 551 of universal modular stent graft assembly 500. However, in the example of FIG. 5B, end offset window 580 is substantially an asymmetric oval in shape. In addition, second component 551 of universal modular stent graft assembly 500 includes end-offset window 580 that is offset from distal end 554 of second component 551 of universal modular stent graft assembly 500 by longitudinal distance 581. As discussed in more detail below, offsetting end offset window 580 from distal end 554 of second component 551 of universal modular stent graft assembly 500 by longitudinal distance 581 provides for even greater flexibility in terms of longitudinal positioning of end offset window 580. In one example, longitudinal distance 581 is on the order of 0.1 inch to 3.0 inches or more, however, those of skill in the art will readily recognize that longitudinal distance 581 can be chosen to be virtually any value according to the needs of the manufacturer and the end user where sometimes circumferentially supporting stent rings are provided.

As discussed above, those of skill in the art will readily recognize that while, end offset window 580 is described above as substantially an asymmetric oval in shape, end offset window 580 can be constructed in any shape desired, including but not limited to, circular, oval, square, diamond, or asymmetric.

FIG. 5C shows second component 551 coupled with first component 501 to form universal modular stent graft assembly 500. As shown in FIG. 5C, universal modular stent graft assembly 500 is substantially similar to universal modular stent graft assembly 100 discussed above with respect to FIG. 1E to FIG. 1K and includes all of the features discussed above with respect to universal modular stent graft assembly 100. Therefore, the description above with respect to universal modular stent graft assembly 100 and FIGS. 1A to 1K is incorporated by reference here to universal modular stent graft assembly 500. However, as discussed above, second component 551 of universal modular stent graft assembly 500 includes end offset window 580 offset from distal end 554 of second component 551 of universal modular stent graft assembly 500 by longitudinal distance 581 and end offset window 580 is substantially an asymmetric oval in shape.

As seen in FIGS. 5C and 5D, as with universal modular stent graft assembly 100, a longitudinal dimension, or length, 587 (FIG. 5C)/597 (FIG. 5D) of the resulting adjustable collateral opening 584 in universal modular stent graft assembly 500, and the longitudinal positioning of adjustable collateral opening 584, is variable and can be adjusted as described above with respect to FIG. 1E and FIG. 1K. However, since end offset window 580 is offset from distal end 554 (FIG. 5B) of second component 551 of universal modular stent graft assembly 500 by longitudinal distance 581, adjustable collateral opening 584 (FIG. 5C) can be longitudinally offset by the additional distance 581. Consequently, universal modular stent graft assembly 500 has additional longitudinal flexibility and application.

FIG. 6A is a side perspective-like view of a first component 601 of a reinforced universal modular stent graft assembly 600 in one embodiment in accordance with the present invention. As shown in FIG. 6A, first component 601 of a reinforced universal modular stent graft assembly 600 is substantially similar to first component 101 of universal modular stent graft assembly 100 discussed above with respect to FIG. 1A and includes all of the features discussed above with respect to first component 101 of universal modular stent graft assembly 100. Therefore, the description above with respect to first component 101 of universal modular stent graft assembly 100 and FIG. 1A is incorporated by reference here to first component 601 of reinforced universal modular stent graft assembly 600.

As shown in FIG. 6A, in one example, first component 601 of reinforced universal modular stent graft assembly 600 is a substantially circular cylinder and includes a proximal, e.g., first, end 602 and a distal, e.g., second, end 604 connected by a generally circularly cylindrical body 606.

In one example, distal end 604 is substantially circularly cylindrical, body 606 is substantially circularly cylindrical and distal end 604 and body 606 have the same diameter D. However, in alternative embodiments, body 606 has a diameter greater than or less than the diameter of distal end 604.

As shown in FIG. 6A, body 606 of first component 601 of reinforced universal modular stent graft assembly 600 includes a stent body mesh 608 made of stainless steel, nitinol, or other similar materials, adapted to render first component 601 of reinforced universal modular stent graft assembly 600 flexible and, as well, capable of being reduced in dimension for insertion into various delivery devices such as a catheter or lumen and attendant balloon (not shown). As discussed above, these delivery systems are well known in the art. Moreover, as also discussed above, it is also well-known in the art to construct stented grafts of various materials such as stainless steel or nitinol, capable of being reduced in size by stress or temperature and, upon delivery to a diseased artery, capable of being reformed to their original size and shape.

As shown in FIG. 6A, body 606 of first component 601 of reinforced universal modular stent graft assembly 600 also includes a graft 610 comprised of a hollow tube of material, such as Dacron, that is typically sewn into position or expanded through the use of a stented balloon catheter (not shown) such that stent body mesh 608 and graft 610 are coupled to form the hollow tubular structure making up body 606. However, as also shown in FIG. 6A, a reinforcement mesh 660 alone covers first component window 620.

In FIG. 6A, for illustrative purposes, reinforcement mesh 660 is drawn in such a way to distinguish reinforcement mesh 660 from stent body mesh 608, graft 610 and body 606. However, in one example, reinforcement mesh 660 is simply a continuation of stent body mesh 608 and is, therefore, also made of stainless steel, nitinol, or other similar materials. In this example, first component window 620 is formed by simply not covering, or cutting away, the portion (not shown) of graft 610 that would normally cover first component window 620. In another example, reinforcement mesh 660 is a mesh formed separately from stent body mesh 608.

The inclusion of reinforcement mesh 660 to cover first component window 620 has several advantages. First, when first component window 620 is formed by simply not covering, or cutting away, the portion (not shown) of graft 610 that would normally cover first component window 620, production of first component 601 of reinforced universal modular stent graft assembly 600 is simplified. In addition, reinforcement mesh 660 makes the structure of first component 601 of reinforced universal modular stent graft assembly 600 sturdier and less susceptible to deformation, i.e., reinforcement mesh 660 reinforces first component 601 of reinforced universal modular stent graft assembly 600.

In one example, first component window 620 is a circular cylindrical portion. However, while first component window 620 is described above, and shown in FIG. 6A, as a substantially rectangular lateral opening with substantially straight longitudinal window perimeter side 622, those of skill in the art will readily recognize that second component window 620 can be constructed in any shape desired, including but not limited to, circular, oval, square, diamond, or asymmetric.

In addition, those of skill in the art will recognize that, although first component 601 of reinforced universal modular stent graft assembly 600 is described above as being generally cylindrical, in an alternative embodiment, first component 601 of reinforced universal modular stent graft assembly 600 is eccentric, i.e., non cylindrical.

FIG. 6B is a side perspective-like view of a second component 651 of reinforced universal modular stent graft assembly 600 in one embodiment in accordance with the present invention. As shown in FIG. 6B, second component 651 of reinforced universal modular stent graft assembly 600 is substantially similar to second component 151 of universal modular stent graft assembly 100 discussed above with respect to FIG. 1B and includes substantially all of the features discussed above with respect to second component 151 of universal modular stent graft assembly 100. Therefore, the description above with respect to second component 151 of universal modular stent graft assembly 100 and FIG. 1B is incorporated by reference here to second component 651 of reinforced universal modular stent graft assembly 600. However, in the example of FIG. 6B, end offset window 680 is substantially an asymmetric oval in shape. In addition, second component 651 of reinforced universal modular stent graft assembly 600 includes an end-offset window 680 that is offset from distal end 664 of second component 651 of universal modular stent graft assembly 600 by longitudinal distance 681. As discussed in more detail above, offsetting end offset window 680 from distal end 664 of second component 651 of universal modular stent graft assembly 600 by longitudinal distance 681 provides for even greater flexibility in terms of longitudinal positioning of end offset window 680.

As discussed above, those of skill in the art will readily recognize that while, end offset window 680 is described above as substantially an asymmetric oval in shape, end offset window 680 can be constructed in any shape desired, including but not limited to, circular, oval, square, diamond, or asymmetric.

As shown in FIG. 6B, body 656 of second component 651 of reinforced universal modular stent graft assembly 600 includes a stent body mesh 668 made of stainless steel, nitinol, or other similar materials, adapted to render second component 651 of reinforced universal modular stent graft assembly 600 flexible and, as well, capable of being reduced in dimension for insertion into various delivery devices such as a catheter or lumen and attendant balloon (not shown). As discussed above, these delivery systems are well known in the art. Moreover, as also discussed above, it is also well-known in the art to construct stented grafts of various materials such as stainless steel or nitinol, capable of being reduced in size by stress or temperature and, upon delivery to a diseased artery, capable of being reformed to their original size and shape.

As shown in FIG. 6B, body 656 of second component 651 of reinforced universal modular stent graft assembly 600 also includes a graft 650, comprised of a hollow tube of material, such as Dacron, that is typically sewn into position or expanded through the use of a stented balloon catheter (not shown) such that stent body mesh 668 and graft 650 are coupled to form the hollow tubular structure making up body 656. However, as also shown in FIG. 6B, a reinforcement mesh 661, or elements of a ring spring, alone cover second component window 680.

In FIG. 6B, for illustrative purposes, reinforcement mesh 680 is drawn in such a way to distinguish reinforcement mesh 661 from stent body mesh 668, graft 650 and body 656. However, in one example, reinforcement mesh 651 is simply an extension of stent body mesh 668 and is, therefore, also made of stainless steel, nitinol, or other similar materials. In this example, second component window 680 is formed by simply not covering, or cutting away, the portion (not shown) of graft 650 that would normally cover first component window 680. In another example, reinforcement mesh 661 is a mesh formed separately from stent body mesh 668.

As with reinforcement mesh 660 discussed above, the inclusion of reinforcement mesh 661 to cover second component window 680 has several advantages. First, when second component window 680 is formed by simply not covering, or cutting away, the portion (not shown) of graft 650 that would normally cover second component window 680, production of second component 651 of reinforced universal modular stent graft assembly 600 is simplified. In addition, reinforcement mesh 661 makes the structure of second component 651 of reinforced universal modular stent graft assembly 600 sturdier and less susceptible to deformation.

FIG. 6C shows second component 651 coupled with first component 601 to form reinforced universal modular stent graft assembly 600 with adjustable collateral opening 684. As shown in FIG. 6C, reinforced universal modular stent graft assembly 600 is substantially similar to universal modular stent graft assembly 100 discussed above with respect to FIG. 1E to FIG. 1K and includes all of the features discussed above with respect to universal modular stent graft assembly 100. Therefore, the description above with respect to universal modular stent graft assembly 100 and FIGS. 1A to 1K is incorporated by reference here to universal modular stent graft assembly 600.

As discussed above, the longitudinal dimension, or length, of the adjustable collateral openings of the universal modular stented graft assemblies of the invention is adjustable and the longitudinal positioning of the openings is also adjustable. In addition, the radial dimension, or width, of the adjustable collateral openings of the universal modular stented graft assemblies of the invention is also adjustable, as is the radial positioning of the adjustable collateral openings. Consequently, as discussed above, and in contrast to prior art methods and structures, the universal modular stented graft assemblies of the invention do not need to be custom made for each patient. Therefore, the universal modular stented graft assemblies of the invention can be mass-produced with minimal labor costs.

In addition, using the universal modular stented graft assemblies of the invention, it is not necessary to obtain the exact measurements that were required to build the custom stented graft structures used with prior art techniques such as Taheri '824. Consequently, there is less opportunity to introduce human error in both the measurement taking process and the implementing of those measurements during production/assembly/deployment.

In addition, in contrast to the prior art, using the universal modular stented graft assemblies of the invention, there is no time lag since the universal modular stented graft assemblies of the invention can be kept in inventory and assembled on site and adjusted as needed.

This disclosure provides exemplary embodiments in accordance with the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A universal modular stent graft assembly comprising:
   a first component, said first component comprising:
   a first component proximal end with a first component proximal end opening;
   a first component distal end with a first component distal end opening;
   a first component body comprising a graft connecting said first component proximal end and said first component distal end; and
   a first component lateral opening formed in said first component body extending from the proximal most end of said first component proximal end, said first component lateral opening defined by a first longitudinal edge of said first component body, a second longitudinal edge of said first component body, and a radial edge of said first component body extending between said first longitudinal edge and said second longitudinal edge;
   a second component, said second component comprising:
   a second component proximal end with a second component proximal end opening;
   a second component distal end with a second component distal end opening;
   a second component body comprising a graft connecting said second component proximal end and said second component distal end; and
   a second component lateral opening formed in said second component body extending from the distal most end of said second component distal end, said second component lateral opening defined by a first longitudinal edge of said second component body, a second longitudinal edge of said second component body, and a radial edge of said second component body extending between said first longitudinal edge of said second component body and said second longitudinal edge of said second component body;
   said second component distal end and at least a portion of said second component body being positioned within said first component proximal end and at least a portion of said first component body to form said universal modular stent graft assembly, said universal modular stent graft assembly being cylindrical and having a proximal end defined by said second component proximal end of said second component and a distal end defined by said first component distal end of said first component; and
   an overlap of said second component lateral opening and said first component lateral opening forming a single collateral opening in said universal modular stent graft assembly offset from and in between said proximal end and said distal end of said universal modular stent graft assembly, said second component body covering said first component lateral opening except at said single collateral opening, said first component body covering said second component lateral opening except at said single collateral opening, said single collateral opening being the only collateral opening in said universal modular stent graft assembly.

2. The universal modular stent graft assembly of claim 1, wherein;
   said single collateral opening in said universal modular stent graft assembly has a longitudinal position along a longitudinal axis of said universal modular stent graft assembly that is adjustable by moving said second component of said universal modular stent graft assembly with respect to said first component of said universal modular stent graft assembly along said longitudinal axis of said universal modular stent graft assembly.

3. The universal modular stent graft assembly of claim 2, wherein;
   said single collateral opening in said universal modular stent graft assembly has a longitudinal dimension along a longitudinal axis of said universal modular stent graft assembly that is adjustable by moving said second component of said universal modular stent graft assembly with respect to said first component of said universal modular stent graft assembly along said longitudinal axis of said universal modular stent graft assembly.

4. The universal modular stent graft assembly of claim 3, wherein;
   said single collateral opening in said universal modular stent graft assembly has a radial position about said longitudinal axis of said universal modular stent graft assembly that is adjustable by rotating said second component of said universal modular stent graft assembly with respect to said first component of said universal modular stent graft assembly around said longitudinal axis of said universal modular stent graft assembly.

5. The universal modular stent graft assembly of claim 4, wherein;
   said single collateral opening in said universal modular stent graft assembly has a radial dimension about said longitudinal axis of said universal modular stent graft assembly that is adjustable by rotating said second component of said universal modular stent graft assembly with respect to said first component of said universal modular stent graft assembly around said longitudinal axis of said universal modular stent graft assembly.

6. The universal modular stent graft assembly of claim 5, wherein;
   said first component body connecting said first component proximal end and said first component distal end further comprises a stent body mesh coupled to said graft of said first component body; and
   said second component body connecting said second component proximal end and said second component distal end further comprises a stent body mesh coupled to said graft of said second component body.

7. The universal modular stent graft assembly of claim 6, wherein;
   said first component body connecting said first component proximal end and said first component distal end is substantially circularly cylindrical and said first component proximal end opening is substantially circularly cylindrical with a first diameter; and
   said second component body connecting said second component proximal end and said second component distal end is substantially circularly cylindrical and said second component proximal end opening is substantially circularly cylindrical with a second diameter, further wherein;

said first diameter is greater than said second diameter.

8. The universal modular stent graft assembly of claim 1 further comprising:

a collateral stent graft structure sealing said single collateral opening.

9. A universal modular stent graft assembly comprising:

a first component, said first component comprising:

a first component proximal end with a first component proximal end opening;

a first component distal end with a first component distal end opening;

a first component body comprising a graft connecting said first component proximal end and said first component distal end; and a first component lateral opening formed in said first component body extending from the proximal most end of said first component proximal end, said first component lateral opening defined by a first longitudinal edge of said first component body, a second longitudinal edge of said first component body, and a radial edge of said first component body extending between said first longitudinal edge and said second longitudinal edge;

a second component, said second component comprising:

a second component proximal end with a second component proximal end opening;

a second component distal end with a second component distal end opening;

a second component body comprising a graft connecting said second component proximal end and said second component distal end; and a second component lateral opening formed in said second component body off-set from said distal end of said second component by an off-set distance along a longitudinal axis of said second component body;

said second component distal end and at least a portion of said second component body being positioned within said first component proximal end and at least a portion of said first component body to form said universal modular stent graft assembly, said universal modular stent graft assembly being cylindrical and having a proximal end defined by said second component proximal end of said second component and a distal end defined by said first component distal end of said first component; and an overlap of said second component lateral opening and said first component lateral opening forming a single collateral opening in said universal modular stent graft assembly offset from and in between said proximal end and said distal end of said universal modular stent graft assembly, said second component body covering said first component lateral opening except at said single collateral opening, said first component body covering said second component lateral opening except at said single collateral opening, said single collateral opening being the only collateral opening in said universal modular stent graft assembly.

10. The universal modular stent graft assembly of claim 9, wherein;

said single collateral opening in said universal modular stent graft assembly has a longitudinal position along a longitudinal axis of said universal modular stent graft assembly that is adjustable by moving said second component of said universal modular stent graft assembly with respect to said first component of said universal modular stent graft assembly along said longitudinal axis of said universal modular stent graft assembly.

\* \* \* \* \*